US011926612B2

(12) United States Patent
Runyon et al.

(10) Patent No.: US 11,926,612 B2
(45) Date of Patent: Mar. 12, 2024

(54) HETEROCYCLIC APELIN RECEPTOR (APJ) AGONISTS AND USES THEREOF

(71) Applicant: Research Triangle Institute, Research Triangle Park, NC (US)

(72) Inventors: Scott P. Runyon, Research Triangle Park, NC (US); Rangan Maitra, Research Triangle Park, NC (US); Sanju Narayanan, Research Triangle Park, NC (US); Kenneth S. Rehder, Research Triangle Park, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

(21) Appl. No.: 16/341,597

(22) PCT Filed: Oct. 11, 2017

(86) PCT No.: PCT/US2017/056117
§ 371 (c)(1),
(2) Date: Apr. 12, 2019

(87) PCT Pub. No.: WO2018/071526
PCT Pub. Date: Apr. 19, 2018

(65) Prior Publication Data
US 2019/0322644 A1    Oct. 24, 2019

Related U.S. Application Data

(60) Provisional application No. 62/407,206, filed on Oct. 12, 2016.

(51) Int. Cl.
| | | |
|---|---|---|
| *C07D 233/90* | (2006.01) | |
| *C07D 249/10* | (2006.01) | |
| *C07D 401/04* | (2006.01) | |
| *C07D 401/12* | (2006.01) | |
| *C07D 401/14* | (2006.01) | |
| *C07D 403/12* | (2006.01) | |
| *C07D 417/14* | (2006.01) | |

(52) U.S. Cl.
CPC ......... *C07D 401/12* (2013.01); *C07D 233/90* (2013.01); *C07D 249/10* (2013.01); *C07D 401/04* (2013.01); *C07D 401/14* (2013.01); *C07D 403/12* (2013.01); *C07D 417/14* (2013.01)

(58) Field of Classification Search
CPC .. C07D 233/90; C07D 249/10; C07D 401/12; C07D 401/04; C07D 401/14; C07D 403/12
See application file for complete search history.

(56) References Cited

U.S. PATENT DOCUMENTS

| | | | |
|---|---|---|---|
| 4,795,484 A | 1/1989 | Katsumichi | |
| 5,571,810 A * | 11/1996 | Matsuo | ................. C07D 333/34 |
| | | | 514/369 |
| 5,624,941 A | 4/1997 | Barth et al. | |
| 8,704,001 B2 | 4/2014 | Masse | |
| 10,100,059 B2 | 10/2018 | Runyon et al. | |
| 10,377,718 B2 | 8/2019 | Runyon et al. | |
| 10,954,247 B2 | 3/2021 | Runyon et al. | |
| 2004/0063691 A1* | 4/2004 | Smith | ..................... A61P 19/02 |
| | | | 514/217.09 |
| 2004/0235854 A1 | 11/2004 | Kruse et al. | |
| 2005/0054679 A1 | 3/2005 | Kruse et al. | |
| 2006/0264470 A1* | 11/2006 | Barth | ..................... A61P 13/10 |
| | | | 548/465 |
| 2008/0125409 A1* | 5/2008 | Kanaya | ..................... A61P 7/02 |
| | | | 514/210.18 |

FOREIGN PATENT DOCUMENTS

| | | | | |
|---|---|---|---|---|
| CN | 1556703 | A | 12/2004 | |
| CN | 101519430 | A | 9/2009 | |
| EP | 377457 | A * | 7/1990 | ............. A61P 29/00 |
| EP | 576357 | B1 | 3/1997 | |
| EP | 3526209 | A1 | 8/2019 | |
| JP | S58194866 | A | 11/1983 | |
| JP | S5998004 | A | 6/1984 | |
| JP | 2005504805 | A | 2/2005 | |
| JP | 2005508384 | A | 3/2005 | |
| JP | 2009529540 | A | 8/2009 | |
| JP | 2010500336 | A | 1/2010 | |
| JP | 2014525912 | A | 10/2014 | |
| JP | 2015521193 | A | 7/2015 | |
| JP | 2015524449 | A | 8/2015 | |
| JP | 2017523126 | A | 8/2017 | |
| JP | 2019501899 | A | 1/2019 | |
| RU | 2325382 | C2 | 5/2008 | |
| WO | 03027076 | A2 | 4/2003 | |
| WO | 03040107 | A1 | 5/2003 | |
| WO | 2004026301 | A1 | 4/2004 | |
| WO | 2006043594 | A1 | 4/2006 | |
| WO | 2008017932 | A2 | 2/2008 | |
| WO | 2008098104 | A1 | 8/2008 | |
| WO | 2011005052 | A2 | 1/2011 | |
| WO | 2011156557 | A2 | 12/2011 | |
| WO | 2013014204 | A2 | 1/2013 | |
| WO | 2013178362 | A1 | 12/2013 | |
| WO | 2014023367 | A1 | 2/2014 | |
| WO | 2014053533 | A1 | 4/2014 | |
| WO | 2015188073 | A1 | 12/2015 | |

(Continued)

OTHER PUBLICATIONS

Hershberger et al. Bioorg. Med. Chem. Lett. 2014, 247, 262-267 (Year: 2014).*
CAS Registry No. 1569675-43-9, which entered STN on Mar. 18, 2014 (Year: 2014).*
CAS Registry No. 1580321-28-3, which entered STN on Apr. 4, 2014 (Year: 2014).*

(Continued)

*Primary Examiner* — Matthew P Coughlin
(74) *Attorney, Agent, or Firm* — Barnes & Thornburg LLP

(57) ABSTRACT

This disclosure is directed to agonists of the apelin receptor (APJ) with heterocyclic cores and uses of such agonists.

20 Claims, No Drawings

(56) References Cited

FOREIGN PATENT DOCUMENTS

WO  2015184011 A3  2/2016
WO  2017100558 A1  6/2017

OTHER PUBLICATIONS

CAS Registry No. 1423365-99-4, which entered STN on Mar. 14, 2013 (Year: 2013).*
CAS Registry No. 931620-33-6, which entered STN on Apr. 22, 2007 (Year: 2007).*
CAS Registry No. 1569560-23-1, which entered STN on Mar. 18, 2014 (Year: 2014).*
CAS Registry No. 1578083-00-7, which entered STN on Apr. 1, 2014 (Year: 2014).*
CAS Registry No. 1584603-48-4, which entered STN on Apr. 15, 2014 (Year: 2014).*
CAS Registry No. 1606440-69-0, which entered STN on May 19, 2014 (Year: 2014).*
CAS Registry No. 1833984-41-0, which entered STN on Dec. 21, 2015 (Year: 2015).*
Plummer et al. Bioorg. Med. Chem. Lett. 2005, 15, 1441-1446 (Year: 2005).*
Cho, K-I, et al., "Targeting the cyclophilin domain of ran-binding protein 2 (Ranbp2) with novel small molecules to control the proteostasis of STAT3, mnRNPA2B1 and M-Opsin", ACS Chemical Neuroscience (Aug. 2015), vol. 6, No. 8, pp. 1476-1485.
Dyck, B, et al., "Potent imidazole and triazole CP1 receptor antagonists related to SR141716", Bioorganic & Medicinal Chemistry Letters, (2004), vol. 14, No. 5, pp. 1151-1154.
Supplemental Partial European Search Report for EP 17860899, dated Mar. 30, 2020.
Corresponding Columbian Application No. NC2019/0003590, dated May 29, 2020 (English translation attached).
International Search Report dated Jan. 22, 2018 for PCT/US2017/056117.
Narayanan, Sanju, et al. "Discovery of a novel small molecule agonist scaffold for the APJ receptor", Bioorganic & Medicinal Chemistry, 2016, vol. 24, pp. 3758-3770.
CAS Registry No. 1831835-31-4 which entered STN on Jun. 24, 2016.
CAS Registry No. 1830232-36-4 which entered STN on Jun. 24, 2016.
CAS Registry No. 1938292-99-9 which entered STN on Jun. 24, 2016.
CAS Registry No. 1938533-13-1 which entered STN on Jun. 24, 2016.
Search Report from corresponding Russian Application No. 2019-103873, dated Feb. 3, 2021 (English translation included).
Office Action for Chinese Appln. No. 2017800611929, dated Mar. 24, 2021.
Tiemann et al., "Increasing myocardial contraction and blood pressure in C57BL/6 mice during early postnatal development," Am. J. Physiol. Heart. Circ. Physiol., 2003, 284, pp. H464-H474.
Wang et al., "Expanding the genetic code for biological studies," Chem Biol., 2009, 16(3) pp. 323-336.
Xie, "A chemical toolkit for proteins-an expanded genetic code," Nat. Rev. Mol. Cell Biol., 2006, 7(10) pp. 775-782.
Zhong et al. "Targeting the apelin pathway asa novel therapeutic approach for cardiovascular diseases," Biochimica et Biophysica Acta, 2017, 1863, 1942-50.
Zou, M.X. et al., "Apelin peptides block the entry of human immunodeficiency virus (HIV)," FEBS Lett., 2000, 473(1) pp. 15-18.
CAS Nos. 1415511-09-09.
CAS Nos. 1415511-07-7.
Sorli, S. Caroline, et al. "Therapeutic potential of interfering with apelin signalling." Drug discovery today Nov. 23-24, 2006: 1100-1106.
Fan, Xiao-Fang, et al. "The Apelin-APJ axis is an endogenous counterinjury mechanism in experimental acute lung injury." Chest 147.4 (2015): 969-978.

* cited by examiner

HETEROCYCLIC APELIN RECEPTOR (APJ) AGONISTS AND USES THEREOF

CROSS-REFERENCE TO RELATED APPLICATIONS

This application is a National Stage application of International Application No. PCT/US2017/056117, filed Oct. 11, 2017, which claims the benefit of U.S. Provisional Patent Application No. 62/407,206, filed Oct. 12, 2016, the entire contents of which are hereby incorporated herein by reference.

1. FIELD

This disclosure relates generally to the discovery of agonists of the apelin receptor (APJ) and uses of such agonists.

2. BACKGROUND

2.1. Introduction: Apelin and the Apelin Receptor (APJ)

The apelin receptor (APJ) was cloned in 1993 as an orphan G-protein coupled receptor (GPCR). The human APJ gene is located on the long arm of chromosome 11 and encodes a 377 amino acid G protein-coupled receptor. The gene for APJ was designated angiotensin-receptor like 1 (AGTRL1) due to sequence similarities between the two receptors. Carpene et al., J Physiol Biochem. 2007; 63(4): 359-373. However, none of the known peptidergic ligands for the angiotensin receptors, including angiotensin, activate APJ. APJ remained an orphan GPCR until 1998 when the peptide apelin was identified as its endogenous ligand. Lee et al., J Neurochem. 2000; 74(1):34-41; Habata et al., Biochim Biophys Acta. 1999; 1452(1):25-35.

Over the years, apelin and APJ have emerged as an important regulator of various physiological processes. Both apelin and APJ are expressed in the central nervous system (CNS) and peripherally in a number of tissues. Expression of APJ has been noted within the vasculature of some organs and is a potent regulator of related processes including angiogenesis and vasoconstriction. Cobellis et al. report increased of expression levels of both apelin and APJ receptor in preeclampsia-complicated pregnancies. Cobellis et al., Histol Histopathol. 2007; 22(1):1-8. APJ is also expressed in nonvascular cell types in heart, liver, and CNS where its primary role is currently under investigation. Medhurst et al., J Neurochem. 2003; 84(5):1162-1172. Apelin and APJ are often co-localized within the same organ suggesting an autocrine regulation of the receptor by its ligand. However, apelin has since been detected in blood suggesting that concomitant paracrine regulation of the receptor is also possible. The apelin-APJ system has been implicated as a regulator of various physiological functions and is believed to play an important role in thermoregulation, immunity, glucose metabolism, angiogenesis, fluid homeostasis, cardiac function, hepatic function and renal function. Ladeiras-Lopes et al., Arq Bras Cardiol. 2008; 90(5):343-349. APJ also acts as a co-receptor during HIV infection. O'Donnell et al., J Neurochem. 2007; 102(6): 1905-1917; Zou et al., FEBS Lett. 2000; 473(1):15-18.

Expression of apelin and APJ are either up- or down-regulated in various pathophysiological conditions. In particular, the APJ appears to be an emerging target for the treatment of cardiovascular failure, liver fibrosis, cancer, angiopathies, pancreatitis, and as a prophylactic against HIV infection. In 2011 Andersen et al. reviewed apelin and APJ as an opportunity for therapeutic uses for pulmonary hypertension and pulmonary arterial hypertension (PAH). Andersen et al. Pulm. Circ. 2011; 1(3) 334-346.

Unfortunately, small molecule ligands of the APJ having suitable pharmacological properties are lacking. Few non-peptide ligand systems has been reported to date. Iturrioz et al. report compounds that contain polycyclic fluorophores, such as lissamine, which make them ill-suited for pharmaceutical uses. Iturrioz et al., FASEB J. 2010; 24:1506-1517; EP 1903052 (Llorens-Cortes et al.). US Publ. Pat. Appn. 2014/0094450 (Hachtel et al.) discloses benzoimidazole-carboxylic acid amide derivatives as APJ receptor modulators.

Accordingly, there is a need for small molecule agonists of APJ.

3. SUMMARY OF THE DISCLOSURE

In particular non-limiting embodiments, the present disclosure provides a compound represented by the Formula I:

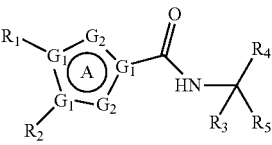

I or a pharmaceutically acceptable salt, a prodrug, or a salt of a prodrug, wherein ring A is a 5-member heteroaryl ring; each $G_1$ is independently selected from C or N; each $G_2$ is independently selected from CH or N; the bond between each two instances of $G_1$ or $G_2$ is either a single or a double bond so as to make the ring A an aromatic heterocycle, wherein at least one $G_1$ or $G_2$ is N and a maximum number of three instances of either $G_1$ or $G_2$ in the ring are simultaneously N; provided that if there are two N in ring A and $G_1$ connected to $R_2$ is N, the adjacent $G_2$ is not N; $R_1$ is represented by the formula:

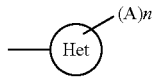

wherein

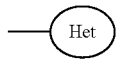

is a monocyclic aryl or heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, $-CF_3$, $-(CH_2)_xNR_7R_8$, $-CN$, $-CONR_7R_8$, $-COR_7$, $-CO_2(CH_2)_xNR_7R_8$, $-CO_2R_7$, halogen, hydroxyl, $-N_3$, $-NHCOR_7$, $-NHSO_2C_{1-8}$ alkyl, $-NHCO_2C_{1-8}$ alkyl, $-NO_2$, $-NR_7R_8$, $-O(CH_2)_xNR_7R_8$, $-O(CH_2)_xCO_2R_7$, $-OCOC_{1-8}$ alkyl, $-OCO(CH_2)_xNR_7R_8$, $-SO_2NR_7R_8$, $-SO_{1-3})R_7$, or $-SR_7$; $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-s}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —(CH$_2$)$_x$CONHR$_9$, —(CH$_2$)$_x$COR$_9$, —(CH$_2$)$_x$CO$_2$R$_9$, H, or heteroaryl; or R$_7$ and R$_8$ together make a 3-9 member ring which may contain one or more heteroatoms; or R$_7$ and R$_8$ together make a 5-8 nitrogen containing member ring with one or more carbonyl groups; n is 1, 2, 3, 4 or 5; R$_2$ is optionally substituted C$_{3-8}$ alkyl or optionally substituted C$_{0-8}$ alkyl-R$_{10}$, wherein R$_{10}$ is a 3- to 8-membered ring, optionally containing one or more heteroatom selected from N, O, or S, optionally containing one or more degrees of unsaturation; R$_3$ is H; R$_4$ and R$_5$ are independently adamantanyl, aryl, C$_{1-8}$ alkyl, C$_{1-8}$ alkyl alcohol, C$_{1-8}$ alkyl amino, C$_{1-8}$ alkyl amido, C$_{2-8}$ alkyl(aryl), C$_{1-8}$ alkyl (C$_{3-8}$ cycloalkyl), C$_{1-8}$ alkyl (C$_{3-8}$ cycloalkyl)-CO$_2$R$_7$, C$_{1-8}$ alkyl guanidinyl, C$_{1-8}$ alkyl heteroaryl, C$_{2-4}$ alkyl heterocycloalkyl, C$_{1-8}$ alkyl thioether, C$_{1-8}$ alkyl thiol, C$_{2-8}$ alkenyl, C$_{2-8}$ alkenyl(aryl), C$_{2-8}$ alkenyl(heteroaryl), C$_{3-8}$ alkynyl, C$_{3-8}$ cycloalkyl, C$_{3-8}$ cycloalkyl-CO$_2$R$_7$, —(CH$_2$)$_x$NR$_7$R$_8$, —(CH$_2$)$_x$OR$_7$, —(CH$_2$)$_x$NR$_9$COR$_7$, —(CH$_2$)$_x$NR$_9$SO$_2$R$_7$, —(CH$_2$)$_x$NR$_9$CO$_2$R$_7$, —(CH$_2$)$_x$NHCOR$_7$, —(CH$_2$)$_x$NHSO$_2$R$_7$, —(CH$_2$)$_x$NHCO$_2$R$_7$, —(CH$_2$)$_x$CONR$_7$R$_8$, —(CH$_2$)$_x$CONR$_7$(CH$_2$)$_y$CO$_2$R$_9$, —(CH$_2$)$_x$CONR$_7$(CH$_2$)$_y$CONR$_7$R$_8$, —(CH$_2$)$_x$CONR$_7$(CH$_2$)$_y$R$_9$, —(CH$_2$)$_x$CO$_7$, —(CH$_2$)$_x$CO$_2$R$_7$, —(CH$_2$)$_x$SO$_2$NR$_7$(CH$_2$)$_y$R$_9$, —CHR$_7$COR$_9$, —CHR$_7$CONHCHR$_8$COR$_9$, —CONR$_7$R$_8$, —CONR$_7$(CH$_2$)$_x$CO$_2$R$_8$, —CONRCHR$_8$CO$_2$R$_9$, —CO$_2$R$_9$, H, or —NHCO$_2$R$_7$; —(CH$_2$)$_x$ SO$_2$NR$_7$R$_8$; or R$_4$ and R$_5$ together make a 4-8 member ring which may be substituted with one or more heteroatoms; or R$_4$ and R$_5$ together make a 5-8 nitrogen containing member ring with one or more carbonyl groups; R$_9$ is aryl, C$_{1-8}$ alkoxy, C$_{1-8}$ alkyl, C$_{1-8}$ alkyl(aryl), C$_{3-8}$ cycloalkyl, H, heteroaryl, or hydroxyl; each x is independently 0-8; and each y is independently 1-8.

A compound represented by the Formula II:

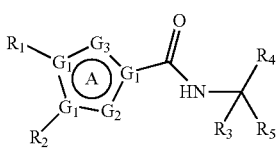

II or a pharmaceutically acceptable salt, a prodrug, or a salt of a prodrug, wherein ring A is a 5-member heteroaryl ring; each G$_1$ is independently selected from C or N; each G$_2$ or G$_3$ is independently selected from CH, N, O or S; wherein at least one G$_2$ or G$_3$ is O or S; if G$_2$ is O or S then, G$_3$ is CH or N; if G$_3$ is O or S then, G$_2$ is CH or N; the bond between each two instances of G$_1$, G$_2$ or G$_3$ is either a single or a double bond so as to make the ring A an aromatic heterocycle, and a maximum number of two instances of either G$_1$ G$_2$ or G$_3$ in the ring are simultaneously N; R$_1$ is represented by the formula:

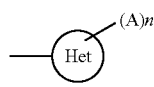

wherein

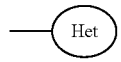

is a monocyclic aryl or heteroaryl group; each A is independently C$_{1-8}$ alkyl, C$_{1-8}$ alkyl(aryl), C$_{1-8}$ alkoxy, C$_{1-8}$ alkoxy aryl, C$_{2-8}$ alkenyl, C$_{3-8}$ alkynyl, C$_{3-8}$ cycloalkyl, —CF$_3$, —(CH$_2$)$_x$NR$_7$R$_8$, —CN, —CONR$_7$R$_8$, —COR$_7$, —CO$_2$(CH$_2$)$_x$NR$_7$R$_8$, —CO$_2$R$_7$, halogen, hydroxyl, —N$_3$, —NHCOR$_7$, —NHSO$_2$C$_{1-8}$ alkyl, —NHCO$_2$C$_{1-8}$ alkyl, —NO$_2$, —NR$_7$R$_8$, —O(CH$_2$)$_x$NR$_7$R$_8$, —O(CH$_2$)$_x$CO$_2$R$_7$, —OCOC$_{1-8}$ alkyl, —OCO(CH$_2$)$_x$NR$_7$R$_8$, —SO$_2$NR$_7$R$_8$, —SO$_{(1-3)}$R$_7$, or —SR$_7$; R$_7$ and R$_8$ are independently C$_{1-8}$ alkoxy, aryl, C$_{1-8}$ alkyl, C$_{1-8}$ alkyl alcohol, C$_{1-8}$ alkyl amino, C$_{1-8}$ alkyl amido, C$_{1-8}$ alkyl(aryl), C$_{1-8}$ alkyl (C$_{3-8}$ cycloalkyl), C$_{1-8}$ alkyl guanidinyl, C$_{1-8}$ alkyl heteroaryl, C$_{1-8}$ alkyl thioether, C$_{1-8}$ alkyl thiol, C$_{2-8}$ alkenyl, C$_{3-8}$ alkynyl, C$_{3-8}$ cycloalkyl, —(CH$_2$)$_x$CONHR$_9$, —(CH$_2$)$_x$COR$_9$, —(CH$_2$)$_x$CO$_2$R$_9$, H, or heteroaryl; or R$_7$ and R$_8$ together make a 3-9 member ring which may contain one or more heteroatoms; or R$_7$ and R$_8$ together make a 5-8 nitrogen containing member ring with one or more carbonyl groups; n is 1, 2, 3, 4 or 5; R$_2$ is optionally substituted C$_{3-8}$ alkyl or optionally substituted C$_{0-8}$ alkyl-R$_{10}$, wherein R$_{10}$ is a 3- to 8-membered ring, optionally containing one or more heteroatom selected from N, O, or S, optionally containing one or more degrees of unsaturation; R$_3$ is H; R$_4$ and R$_5$ are independently adamantanyl, aryl, C$_{1-8}$ alkyl, C$_{1-8}$ alkyl alcohol, C$_{1-8}$alkyl amino, C$_{1-8}$ alkyl amido, C$_{2-8}$ alkyl(aryl), C$_{1-8}$ alkyl (C$_{3-8}$ cycloalkyl), C$_{1-8}$ alkyl (C$_{3-8}$ cycloalkyl)-CO$_2$R$_7$, C$_{1-8}$ alkyl guanidinyl, C$_{1-8}$ alkyl heteroaryl, C$_{2-4}$ alkyl heterocycloalkyl, C$_{1-8}$ alkyl thioether, C$_{1-8}$ alkyl thiol, C$_{2-8}$ alkenyl, C$_{2-8}$ alkenyl(aryl), C$_{2-8}$ alkenyl(heteroaryl), C$_{3-8}$ alkynyl, C$_{3-8}$ cycloalkyl, C$_{3-8}$ cycloalkyl-CO$_2$R$_7$, —(CH$_2$)$_x$NR$_7$R$_8$, —(CH$_2$)$_x$OR$_7$, —(CH$_2$)$_x$NR$_9$COR$_7$, —(CH$_2$)$_x$NR$_9$SO$_2$R$_7$, —(CH$_2$)$_x$NR$_9$CO$_2$R$_7$, —(CH$_2$)$_x$NHCOR$_7$, —(CH$_2$)$_x$NHSO$_2$R$_7$, —(CH$_2$)$_x$NHCO$_2$R$_7$, —(CH$_2$)$_x$CONR$_7$R$_8$, —(CH$_2$)$_x$CONR$_7$(CH$_2$)$_y$CO$_2$R$_9$, —(CH$_2$)$_x$CONR$_7$(CH$_2$)$_y$CONR$_7$R$_8$, —(CH$_2$)$_x$CONR$_7$(CH$_2$)$_y$R$_9$, —(CH$_2$)$_x$COR$_7$, —(CH$_2$)$_x$CO$_2$R$_7$, —(CH$_2$)$_x$SO$_2$NR$_7$(CH$_2$)$_y$R$_9$, —CHR$_7$COR$_9$, —CHR$_7$CONHCHR$_8$COR$_9$, —CONR$_7$R$_8$, —CONR$_7$(CH$_2$)$_x$CO$_2$R$_8$, —CONR$_7$CHR$_8$CO$_2$R$_9$, —CO$_2$R$_9$, H, or —NHCO$_2$R$_7$; —(CH$_2$)$_x$ SO$_2$NR$_7$R$_8$; or R$_4$ and R$_5$ together make a 4-8 member ring which may be substituted with one or more heteroatoms; or R$_4$ and R$_5$ together make a 5-8 nitrogen containing member ring with one or more carbonyl groups; R$_9$ is aryl, C$_{1-8}$ alkoxy, C$_{1-8}$ alkyl, C$_{1-8}$ alkyl(aryl), C$_{3-8}$ cycloalkyl, H, heteroaryl, or hydroxyl; each x is independently 0-8; and each y is independently 1-8.

The compound of the present disclosure, represented by the Formula III:

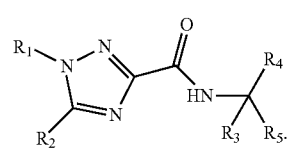

III

The compound of the present disclosure, represented by the Formula IV:

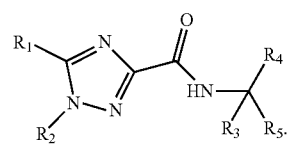

IV

The compound of the present disclosure, represented by the Formula V:

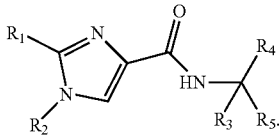

The compound of any of the present disclosure, wherein

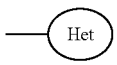

is a monocyclic aryl group; wherein n is 1 or 2; each A is independently $C_{1-4}$ alkoxy, $C_{1-4}$ alkoxy aryl, or halogen; $R_2$ is a substituted aryl, substituted heteroaryl, unsubstituted heteroaryl, $C_{2-8}$ alkyl or $C_{3-8}$ cycloalkyl; $R_4$ is $C_{1-8}$ alkyl, $C_{2-8}$ alkyl(aryl), $C_{1-8}$ alkyl ($C_{3-8}$ cycloalkyl) or —$CO_2R_9$; $R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xC_0NR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7(CH_2)_xCO_2R_8$, or —$CO_2R_9$; $R_6$ is H; $R_9$ is $C_{1-8}$ alkyl, H, or heteroaryl which is an oxazole; x is 1-4; y is 1-3; and Z is =O.

The compound of the present disclosure, wherein n is 1 or 2; each A is independently $C_1$ alkoxy, $C_1$ alkoxy aryl, or halogen; $R_2$ is substituted aryl, unsubstituted heteroaryl, substituted heteroaryl, $C_4$ alkyl or $C_6$ cycloalkyl; $R_4$ is $C_{1-8}$ alkyl, $C_{2-8}$ alkyl(aryl), $C_{1-8}$ alkyl ($C_{3-8}$ cycloalkyl) or —$CO_2R_9$; $R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$CHR_7COR_9$, —$CHR_7CONHCHR_8COR_9$, —$CONR_7R_8$, —$CONR_7(CH_2)_xCO_2R_8$, or —$CO_2R_9$; $R_6$ is H; $R_8$ is $C_{1-4}$ alkyl or H; $R_9$ is $C_{1-8}$ alkyl, H, or heteroaryl which is an oxazole; x is 1-4; y is 1-3; and Z is =O.

The compound of the present disclosure, wherein each A is independently $C_1$-$C_3$ alkoxy, $C_1$-$C_3$ alkyl, chloro, or fluoro.

The compound of the present disclosure, wherein each A is independently fluoro substituted $C_1$-$C_3$ alkoxy or fluoro substituted $C_1$-$C_3$ alkyl.

The compound of the present disclosure, wherein $R_2$ is an optionally substituted 5 or 6 membered heteroaryl ring, —$C_4H_9$, —$C_5H_{11}$, -$cC_4H_8$ or -$cC_5H_{10}$.

The compound of the present disclosure, wherein $R_4$ is $C_{1-8}$ alkyl(aryl), $C_1$-8 alkyl heteroaryl, $C_{2-8}$ alkenyl(aryl), or $C_{2-8}$ alkenyl(heteroaryl).

The compound of the present disclosure, wherein $R_4$ is $C_{1-8}$ alkyl(difluoroaryl), $C_{1-8}$ alkyl difluoro heteroaryl, $C_{2-8}$ alkenyl(difluoro aryl), or $C_{2-8}$ alkenyl(difluoro heteroaryl).

The compound of the present disclosure, wherein $R_8$ is heteroaryl.

The compound of the present disclosure, wherein $R_8$ is oxadiazole, oxazole, n-methyl thiazole, tetrazole, thiazole, or triazole.

The compound of the present disclosure, wherein the compound is (3S)—N-cyclobutyl-3-({5-cyclopentyl-1-[2-(trifluoromethyl)phenyl]-1H-1,2,4-triazol-3-yl}formamido)-5-(piperidin-1-yl)pentanamide, (3S)—N-cyclobutyl-3-({1-cyclopentyl-5-[2-(trifluoromethyl)phenyl]-1H-1,2,4-triazol-3-yl}formamido)-5-(piperidin-1-yl) pentanamide, (3S)—N-cyclobutyl-3-({1-cyclopentyl-5-[2-(trifluoromethyl)phenyl]-1H-1,2,4-triazol-3-yl}formamido)-5-(3,3-difluoropiperidin-1-yl)pentanamide, (3S)—N-cyclobutyl-3-({5-cyclopentyl-1-[2-(trifluoromethyl)phenyl]-1H-1,2,4-triazol-3-yl}formamido)-5-(3,3-difluoropiperidin-1-yl)pentanamide, (3S)-3-({5-cyclopentyl-1-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide, (3S)-3-({1-cyclopentyl-5-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide, (3S)-3-({5-cyclopentyl-1-[2-(trifluoromethyl)phenyl]-1H-1,2,4-triazol-3-yl}formamido)-5-(3,3-difluoropiperidin-1-yl)pentanoic acid, (3S)-3-({1-cyclopentyl-5-[2-(trifluoromethyl)phenyl]-1H-1,2,4-triazol-3-yl}formamido)-5-(3,3-difluoropiperidin-1-yl)pentanoic acid, (3S)—N-cyclobutyl-3-({2-cyclopentyl-1-[2-(trifluoromethyl)phenyl]-1H-imidazol-4-yl) formamido)-5-(3,3-difluoropiperidin-1-yl)pentanamide, (3S)-3-({2-cyclopentyl-1-[2-(trifluoromethyl)phenyl]-1H-imidazol-4-yl}formamido)-5-(3,3-difluoropiperidin-1-yl)-N-methyl-N-(1,3-thiazol-2-yl)pentanamide, (3S)-3-(1-{5-cyclopentyl-1-[2-(trifluoromethyl)phenyl]-1H-1,2,4-triazol-3-yl}-N-methylformamido)-5-(3,3-difluoropiperidin-1-yl)-N-methyl-N-(1,3-thiazol-2-yl)pentanamide, (3S)-3-{[4-(2-chlorophenyl)-1-methyl-5-(2-methylpropyl)-1H-imidazol-2-yl]formamido}-5-(3,3-difluoropiperidin-1-yl)pentanoic acid, (3S)-3-{[4-(2-chlorophenyl)-1-methyl-5-(2-methylpropyl)-1H-imidazol-2-yl]formamido}-5-(3,3-difluoropiperidin-1-yl)-N-methyl-N-(1,3-thiazol-2-yl)pentanamide, (3S)-3-{[4-(2-chlorophenyl)-1-methyl-5-(2-methylpropyl)-1H-imidazol-2-yl]formamido}-N-cyclobutyl-5-(3,3-difluoropiperidin-1-yl)pentanamide, (3S)-3-({1-cyclopentyl-5-[3-(trifluoromethyl)pyridin-2-yl]-1H-1,2,4-triazol-3-yl}formamido)-5-(3,3-difluoropiperidin-1-yl)pentanoic acid, (3S)-3-({5-cyclopentyl-1-[2-(trifluoromethyl)pyridin-3-yl]-1H-1,2,4-triazol-3-yl}formamido)-5-(3,3-difluoropiperidin-1-yl)pentanoic acid, (3S)—N-cyclobutyl-3-({1-cyclopentyl-5-[3-(trifluoromethyl)pyridin-2-yl]-1H-1,2,4-triazol-3-yl} formamido)-5-(3,3-difluoropiperidin-1-yl) pentanamide, (3S)—N-cyclobutyl-3-({5-cyclopentyl-1-[2-(trifluoromethyl)pyridin-3-yl]-1H-1,2,4-triazol-3-yl}formamido)-5-(3,3-difluoropiperidin-1-yl)pentanamide, (3S)—N-cyclobutyl-3-({1-cyclopentyl-5-[2-(trifluoromethyl)pyridin-3-yl]-1H-1,2,4-triazol-3-yl}formamido)-5-(3,3-difluoropiperidin-1-yl)pentanamide, (2S)-2-({5-cyclopentyl-1-[2-(trifluoromethyl)phenyl]-1H-1,2,4-triazol-3-yl}formamido)-N-(2-methoxyethyl)-N-methyl-4-phenylbutanamide, (2S)-2-({1-cyclopentyl-5-[2-(trifluoromethyl)phenyl]-1H-1,2,4-triazol-3-yl}formamido)-N-(2-methoxyethyl)-N-methyl-4-phenylbutanamide, (3S)-3-({5-cyclopentyl-1-[2-(trifluoromethyl)phenyl]-1H-1,2,4-triazol-3-yl}formamido)-5-(3,3-difluoropyrrolidin-1-yl)pentanoic acid, 5-cyclopentyl-N-[(2S)-4-(3,3-difluoropiperidin-1-yl)-1-(1H-1,2,3,4-tetrazol-5-yl)butan-2-yl]-1-[2-(trifluoromethyl)phenyl]-1H-1,2,4-triazole-3-carboxamide, or (3S)-3-({2-cyclopentyl-1-[2-(trifluoromethyl)phenyl]-1H-imidazol-4-yl}formamido)-5-(3,3-difluoropiperidin-1-yl) pentanoic acid.

A pharmaceutical composition comprising at least one pharmaceutically acceptable excipient and a therapeutically effective amount of the compound of the present disclosure.

The pharmaceutical composition of the present disclosure, wherein the therapeutically effective amount is an amount effective for lowering blood pressure.

The pharmaceutical composition of the present disclosure, wherein the therapeutically effective amount is an amount effective for the treatment of asthma, cardiomyopathy, diabetes, dyslipidemia, hypertension, inflammation, liver disease, metabolic disorder, neurodegenerative disease, obesity, preeclampsia, or renal dysfunction.

The pharmaceutical composition of the present disclosure, wherein the hypertension is pulmonary arterial hypertension.

The pharmaceutical composition of the present disclosure, wherein the liver disease is alcoholic liver disease, toxicant-induced liver disease, or viral-induced liver disease.

The pharmaceutical composition of the present disclosure, wherein the renal dysfunction is polycystic kidney disease.

The pharmaceutical composition of the present disclosure, wherein the therapeutically effective amount is an amount effective to treat a vein-related disorder.

The pharmaceutical composition of the present disclosure, wherein the therapeutically effective amount is an amount effective to treat an angioma, a venous insufficiency, a stasis or a thrombosis.

The pharmaceutical composition of the present disclosure, wherein the therapeutically effective amount is an amount effective to reduce the likelihood of HIV-related neurodegeneration.

The use in a treatment of an apelin receptor (APJ) related disorder of a compound represented by the Formula II:

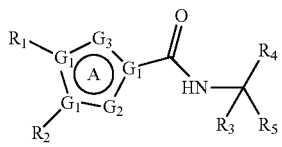

II or a pharmaceutically acceptable salt, a prodrug, or a salt of a prodrug, wherein ring A is a 5-member heteroaryl ring; each $G_1$ is independently selected from C or N; each $G_2$ or $G_3$ is independently selected from CH, N, O or S; wherein at least one $G_2$ or $G_3$ is O or S; if $G_2$ is O or S then, $G_3$ is CH or N; if $G_3$ is O or S then, $G_2$ is CH or N; the bond between each two instances of $G_1$, $G_2$ or $G_3$ is either a single or a double bond so as to make the ring A an aromatic heterocycle, and a maximum number of two instances of either $G_1$ $G_2$ or $G_3$ in the ring are simultaneously N; $R_1$ is represented by the formula:

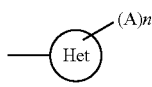

wherein

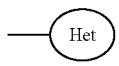

is a monocyclic aryl or heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SO_2NR_7R_8$, —$SO_{1-3})R_7$, or —$SR_7$; $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups; n is 1, 2, 3, 4 or 5; $R_2$ is optionally substituted $C_{3-8}$ alkyl or optionally substituted $C_{0-8}$ alkyl-$R_{10}$, wherein $R_{10}$ is a 3- to 8-membered ring, optionally containing one or more heteroatom selected from N, O, or S, optionally containing one or more degrees of unsaturation; $R_3$ is H; $R_4$ and $R_5$ are independently adamantanyl, aryl, $C_{0-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNR_9COR_7$, —$(CH_2)_xNR_9SO_2R_7$, —$(CH_2)_xNR_9CO_2R_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$(CH_2)_xSO_2NR_7(CH_2)_yR_9$, —$CHR_7COR_9$, —$CHR_7CONHCHR_8COR_9$, —$CONR_7R_8$, —$CONR_7(CH_2)_xCO_2R_8$, —$CONR_7CHR_8CO_2R_9$, —$CO_2R_9$, H, or —$NHCO_2R_7$; —$(CH_2)_x SO_2NR_7R_8$, or $R_4$ and $R_5$ together make a 4-8 member ring which may be substituted with one or more heteroatoms; or $R_4$ and $R_5$ together make a 5-8 nitrogen containing member ring with one or more carbonyl groups; $R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; each x is independently 0-8; and each y is independently 1-8.

The use in a treatment of an apelin receptor (APJ) related disorder of compound represented by the Formula II:

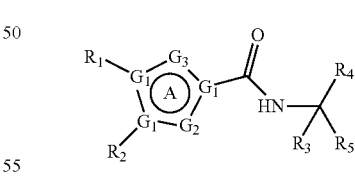

II or a pharmaceutically acceptable salt, a prodrug, or a salt of a prodrug, wherein ring A is a 5-member heteroaryl ring; each $G_1$ is independently selected from C or N; each $G_2$ or $G_3$ is independently selected from CH, N, O or S; wherein at least one $G_2$ or $G_3$ is 0 or S; if $G_2$ is O or S then, $G_3$ is CH or N; if $G_3$ is O or S then, $G_2$ is CH or N; the bond between each two instances of $G_1$, $G_2$ or $G_3$ is either a single or a double bond so as to make the ring A an aromatic heterocycle, and a maximum number of two instances of either $G_1$ $G_2$ or $G_3$ in the ring are simultaneously N; $R_1$ is represented by the formula:

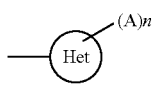

wherein

is a monocyclic aryl or heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_3$-8 alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SO_2NR_7R_8$, —$SO_{(1-3)}R_7$, or —$SR_7$; $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_1$-8 alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups; n is 1, 2, 3, 4 or 5; $R_2$ is optionally substituted $C_{3-8}$ alkyl or optionally substituted $C_{0-8}$ alkyl-$R_{10}$, wherein $R_{10}$ is a 3- to 8-membered ring, optionally containing one or more heteroatom selected from N, O, or S, optionally containing one or more degrees of unsaturation; $R_3$ is H; $R_4$ and $R_8$ are independently adamantanyl, aryl, $C_{1-8}$ alkyl, $C_{1-8}$ alkyl alcohol, $C_{1-8}$ alkyl amino, $C_{1-8}$ alkyl amido, $C_2$-8 alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNR_9COR_7$, —$(CH_2)_xNR_9SO_2R_7$, —$(CH_2)_xNR_9CO_2R_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_xR_9$, —$(CH_2)_xCOR_7$, —$(CH_2)_xCO_2R_7$, —$(CH_2)_xSO_2NR_7(CH_2)_yR_9$, —$CHR_7COR_9$, —$CHR_7CONHCHR_8COR_9$, —$CONR_7R_8$, —$CONR_7(CH_2)_xCO_2R_8$, —$CONR_7CHR_8CO_2R_9$, —$CO_2R_9$, H, or —$NHCO_2R_7$, —$(CH_2)_x$ $SO_2NR_7R_8$; or $R_4$ and $R_8$ together make a 4-8 member ring which may be substituted with one or more heteroatoms; or $R_4$ and $R_5$ together make a 5-8 nitrogen containing member ring with one or more carbonyl groups; $R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; each x is independently 0-8; and each y is independently 1-8.

The use of the present disclosure, wherein the compound has the Formula I, III, IV or V as defined above.

The use of the present disclosure, wherein the apelin receptor (APJ) related disorder is asthma, cardiomyopathy, diabetes, dyslipidemia, hypertension, inflammation, liver disease, metabolic disorder, neurodegenerative disease, obesity, preeclampsia, or renal dysfunction.

The use of the present disclosure, wherein the hypertension is a pulmonary arterial hypertension.

The use of the present disclosure, wherein the liver disease is an alcoholic liver disease, a toxicant-induced liver disease or a viral-induced liver disease.

The use of the present disclosure, wherein the renal dysfunction is a polycystic kidney disease.

The use of the present disclosure, further comprising an α-blocker, an angiotensin converting enzyme (ACE) inhibitor, an angiotensin-receptor blocker (ARB), a β-blocker, a calcium channel blocker, or a diuretic for the treatment of the apelin receptor (APJ) related disorder.

The compound of the present disclosure, for use in a treatment of a vein-related disorder.

The use of the present disclosure, wherein the vein-related disorder is an angioma, a venous insufficiency, a stasis or a thrombosis.

The compound of the present disclosure for use in the treatment to reduce the likelihood of HIV-related neurodegeneration.

4. DETAILED DESCRIPTION OF THE DISCLOSURE

4.1. Definitions

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments from 2 to 8 carbon atoms.

"Alkoxy" refers to a radical—OR where R represents an alkyl, alkyl, cycloalkyl, aryl, or heteroaryl group as defined herein. Representative examples include, but are not limited to, methoxy, ethoxy, propoxy, butoxy, cyclohexyloxy, and the like. The alkoxy group may be substituted or unsubstituted.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with a halogen(s) such as difluoro or trifluoro. In certain embodiments, an alkyl group comprises from 1 to 20 carbon atoms. Alternatively, an alkyl group may comprise from 1 to 8 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1- yl, naphthobenzyl, 2-naphthophenylethan-1-yl and the like. In certain embodiments, an alkyl(aryl) group can be ($C_{6-20}$) alkyl(aryl) e.g., the alkyl group may be ($C_{1-10}$) and the aryl moiety may be ($C_{5-10}$). The alkyl(aryl) group may be substituted or unsubstituted.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen, such as fluorine.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ cycloalkyl, such as, for example, $C_6$ cycloalkyl or $cC_6H_{12}$. The cycloalkyl group may also be a bridged bicyclic cycloalkyl group, a fused cycloalkyl group or a spiro cycloalkyl group. Non-limiting examples of bridged bicyclic cycloalkyl groups are bicyclo[2.2.1]heptane, bicyclo[2.2.1]hexane, bicycle[2.2.2]octane. An example of a fused cycloalkyl group is bicyclo[4.4.0]decane or decalin. Non-limiting examples of spiro cycloalkyl groups are spiro [3.3] heptane, spiro [4.3] octane, or spiro [5.4] decane.

"Disease" refers to any disease, disorder, condition, symptom, or indication.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heterocycloalkyl" refers to a non-aromatic monocyclic ring or fused non-aromatic polycyclic rings with one or more heteroatom(s) independently selected from N, S and O, with the remaining ring atoms being carbon and wherein at least one heteroatom is present in each non-aromatic ring. The heterocycle group may be a three-member ring, a four member ring, a five member ring, a six member ring or a seven member ring. In certain embodiments, the heterocycloalkyl group is 1,4-dioxane, 1,3-dioxolane, 1,4-dithiane, imidazolidine, morpholine, piperidine, piperidone, piperazine, pyrolidone, pyrrolidine, or 1,3,5-trithiane. It may contain an imide. The heterocycloalkyl group may be bicyclic such as an heterospiro compound, e.g., heterospiro [3.3] heptanyl, heterospiro [3.4] octanyl, or heterospiro [5.5] undecanyls. The heterocycloalkyl group may be substituted or unsubstituted. Thus, heterocycloalkyl group encompasses heterocycloalkyl groups substituted with one or more halogens, such as 3,3-difluoropiperidine, or 4,4-difluoropiperidine. In addition, the heterocycloalkyl group may be substituted with a $C_1$-$C_4$ alkyl or $C_1$-$C_4$ halo alkyl group such as a —$CF_3$ group.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Prodrug" refers to a precursor or derivative form of a pharmaceutically active substance that is less bioactive compared to the parent drug and is capable of being enzymatically activated or converted into the more active parent form. Prodrug forms of the compounds described herein may designed to improve bioavailability or stability or reduce toxicity. For example, compounds of the invention having free amino, amido, carboxylic, hydroxyl, or thiol groups can be converted into prodrugs. See Rautio et al., 2008 Nat Rev Drug Dis 7 255-270. For instance, free carboxyl groups can be derivatized as amides, carbamates, esters, or N-Mannich bases. Free hydroxy groups may be derivatized using groups including but not limited to carbonates, dimethylaminoacetates, ethers, hemisuccinates, phosphate esters, and phosphoryloxymethyloxycarbonyls, as outlined in Fleisher et al., 1996 Advanced Drug Delivery Reviews 19, 115-130. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in Robinson et al., 1996 J Med Chem 39 10-18. Free amines can also be derivatized as amides, carbamates, imines, N-Mannich bases, oximes, phosphonamides, or sulfonamides. Carbonyls may be derivatized to imine or oxime prodrugs. Thiols may be derivatized as esters or ethers. Prodrugs may also include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes beta-alanine, citrulline, demosine, gamma-aminobutyric acid, homocysteine, homoserine, 4-hydroxyproline, hydroxylysine, isodemosine, 3-methylhistidine, norvalin, methionine sulfone, and ornithine.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, $CO_2H$, cyano, difluoro, halogen, hydroxyl, $-N_3$, $-NH_2$, $-SO_{1-3}H$, $-SH$, or trifluoro.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Pairs of the functional groups defined herein may be combined in a chemically rational way. For example, $C_1$-$C_8$ alkyl amino means the functional group $C_1$-$C_8$ alkyl, e.g., $-nC_5H_{11}$, is combined with the functional group, amino, e.g., $-NH_2$ to form in this example $-nC_5H_{10}NH_2$. Similarly, $C_1$-$C_8$ alkoxy aryl means the functional group $C_1$-$C_8$ alkoxy, e.g., $-CH_2CH_2OCH_2CH_3$ or $-OCH_2CH_3$ combined with an aryl group, e.g., $-C_6H_5F$ to form $-CH_2CH_2OCH_2CH_2-C_6H_5F$ or $-OCH_2CH_3-C_6H_5F$, respectively.

As used herein the substituents $R_4$, $R_5$, $R_6$, $R_7$, or $R_8$ may independently may be single a, p, y, 6 amino acids, or their corresponding side chains, such as the twenty naturally occurring amino acids, e.g., alanine (Ala/A); arginine (Arg/R); asparagine (Asn/N); aspartic acid (Asp/D); cysteine (Cys/C); glutamic acid (Glu/E); glutamine (Gln/Q); glycine (Gly/G); histidine (His/H); isoleucine (Ile/I); leucine (Leu/L); lysine (Lys/K); methionine (Met/M); phenylalanine (Phe/F); proline (Pro/P); Serine (Ser/S); threonine (Thr/T); tryptophan (Trp/W); tyrosine (Tyr/Y); and valine (Val/V). The individual amino acids may of either the R or the S chirality. Alternatively, $R_4$, $R_5$, $R_6$, $R_7$, or $R_8$ independently may be two or three amino acids linked by a peptide bond. $R_4$, $R_5$, $R_6$, $R_7$, or $R_8$ independently may be dipeptides or tripeptides (Hobbs et al., Proc Nat Acad Sci USA. 1993, 90, 6909-6913); U.S. Pat. No. 6,075,121 (Bartlett et al.) peptoids; or vinylogous polypeptides (Hagihara et al., J Amer Chem Soc. 1992, 114, 6568), the contents of which are hereby incorporated by reference in their entireties. $R_4$, $R_5$, $R_6$, $R_7$, or $R_8$ independently may be part of the extended unnatural amino acids, e.g., Xie and Schultz, Nat Rev Mol Cell Biol. 2006, 7(10):775-82 or Wang et al., Chem Biol. 2009, 16(3):323-36, the contents of which are hereby incorporated by reference in their entireties.

4.2. Deuterated and Other Isotopic Variants

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, 33S, 34S, 35S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Substitution with positron emitting isotopes, such as $^{11}$C, $^{18}$F, $^{15}$O and $^{13}$N, can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. Alternatively, deuterium may be also incorporated into a compound using methods such as through reduction such as using $LiAlD_4$ or $NaBD_3$, catalytic hydrogenation or acidic or basic isotopic exchange using appropriate deuterated reagents such as deuterides, $D_2$ and $D_2O$. In addition to the above, PCT publications, WO2014/169280; WO2015/058067; U.S. Pat. Nos. 8,354,557; 8,704,001 and US Patent Application Publication Nos.; 2010/0331540; 2014/0081019; 2014/0341994; 2015/0299166, the methods are hereby incorporated by reference.

4.3. Synthetic Schemes for Heterocyclic Cores

The compounds described herein may be made by a number of methods known to those skilled in the art. Specific synthetic schemes may be found in the experimental section. See Schemes 1-3 in Section 5.1. Non-limiting methods to synthesize furans, imidazoles, oxazoles, pyrazoles, pyrroles, thiazoles, thiophenes and triazoles are shown below.

4.3.1. Pyrroles

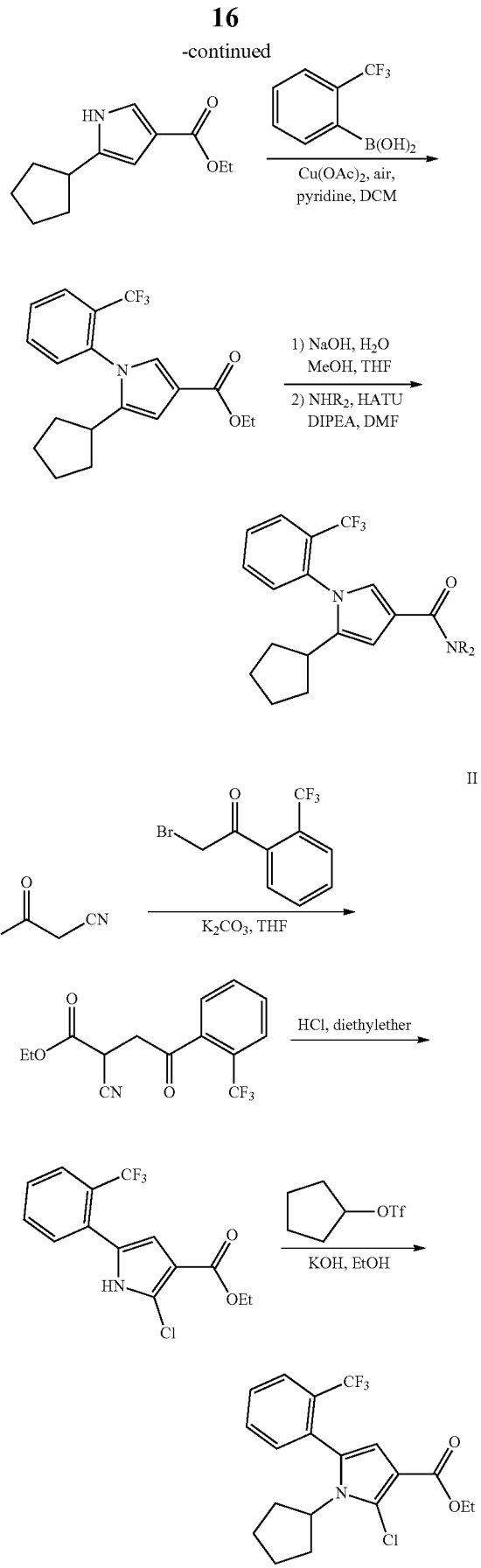

-continued
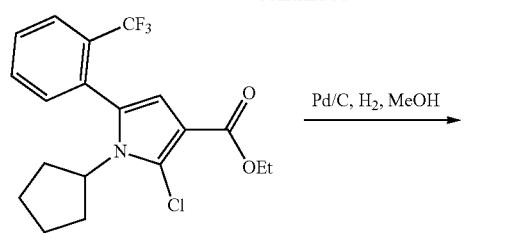
Pd/C, H₂, MeOH
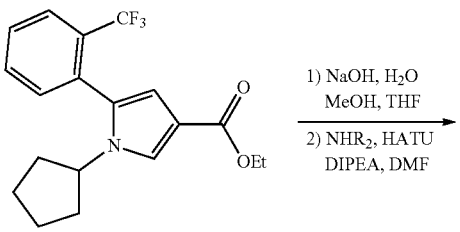
1) NaOH, H₂O
   MeOH, THF
2) NHR₂, HATU
   DIPEA, DMF
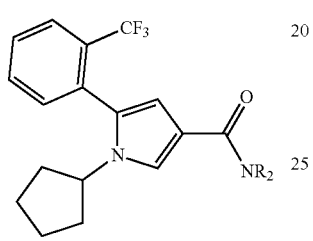
1) NH₂Ph, t-BuNC,
   Ti(dpma)(NMe₂)₂
   Toluene, 100° C.
2) DBU, DMSO, 120° C.
   ClH₃N⁀CO₂Et
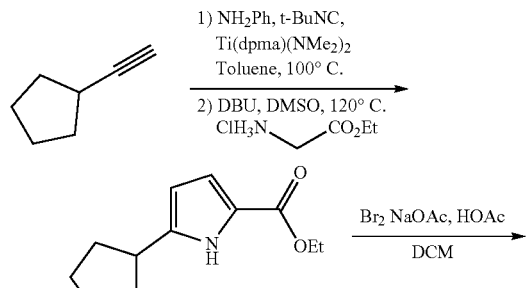
Br₂ NaOAc, HOAc
DCM
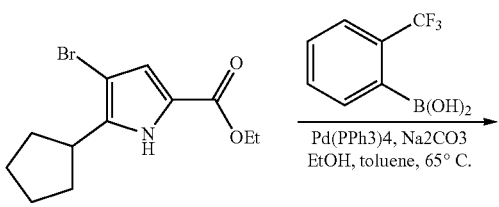
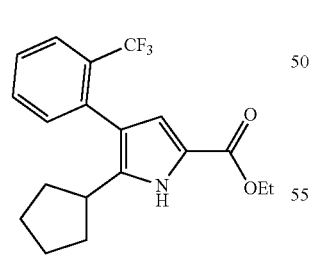 + 2-CF₃-C₆H₄-B(OH)₂
Pd(PPh₃)₄, Na₂CO₃
EtOH, toluene, 65° C.
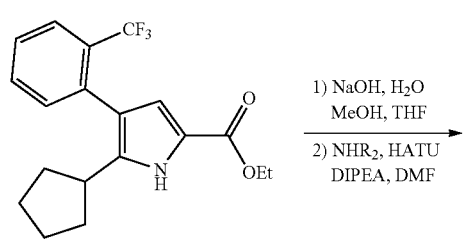
1) NaOH, H₂O
   MeOH, THF
2) NHR₂, HATU
   DIPEA, DMF
-continued
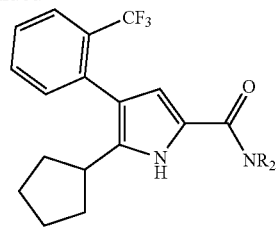
IV
SO₂Tol—NC + 2-CF₃-C₆H₄-CHO
i) t-BuOK, THF, −40° C.
ii)
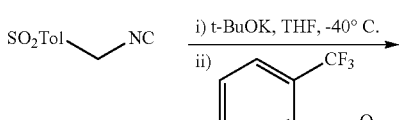
POCl₃, Et₃N, DME
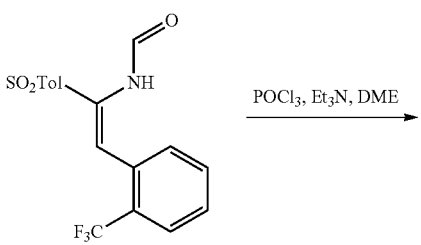 + PhC(O)CH₂-cyclopentyl
t-BuOK, EtOH
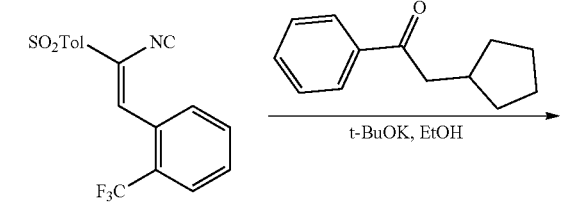
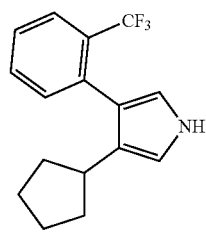 + R—N=C=O
Et₃N, THF
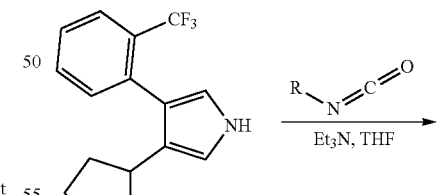
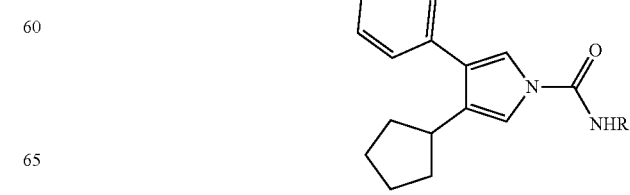
III 19
-continued
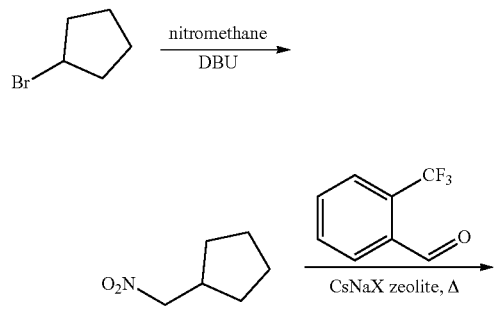
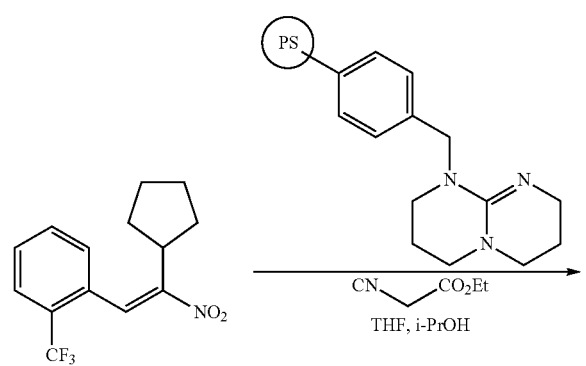
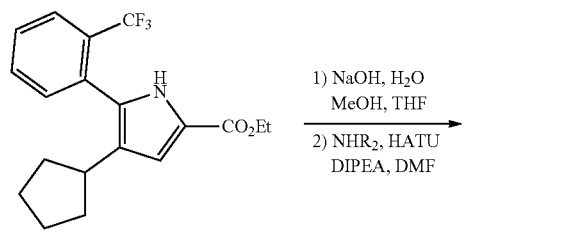
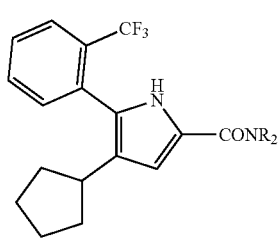
20
4.3.2. Furans
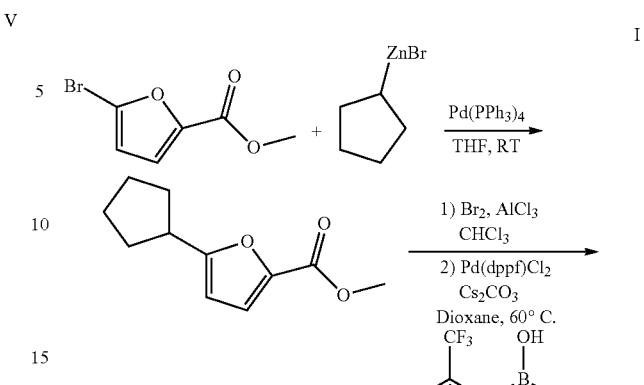
I
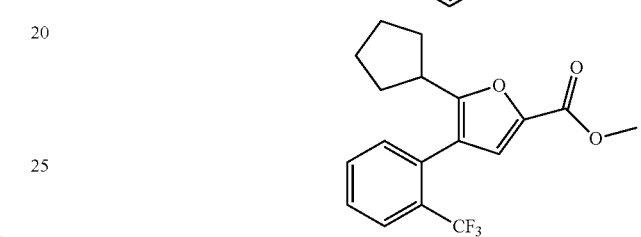
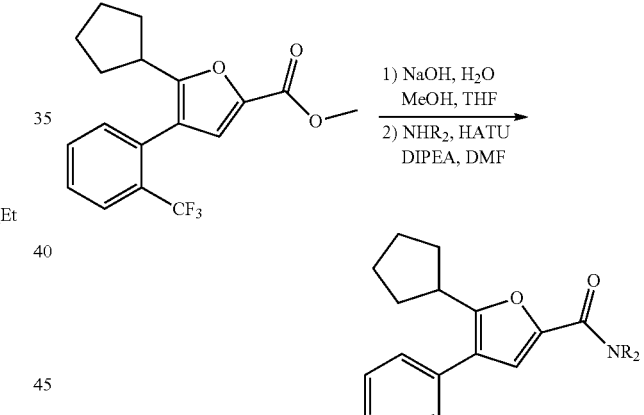
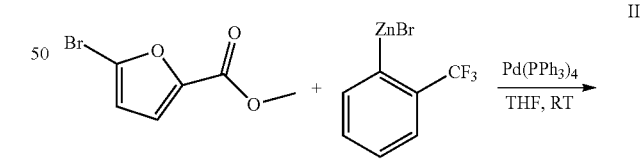
II
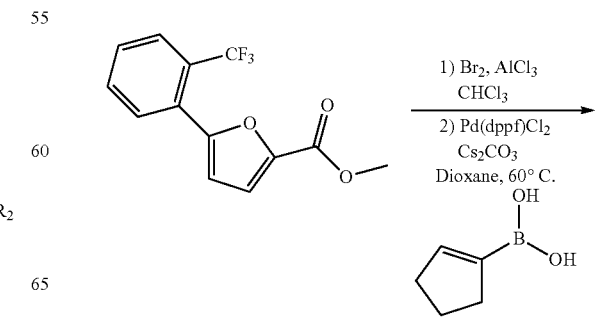

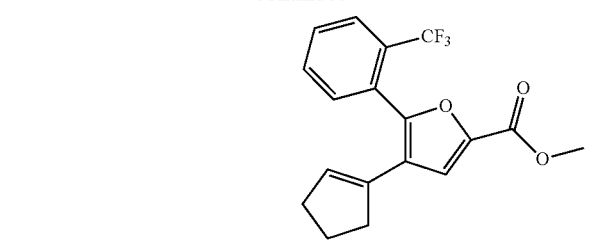
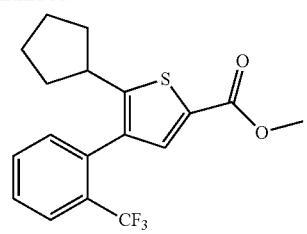
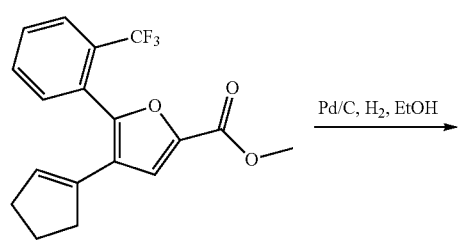
Pd/C, H₂, EtOH
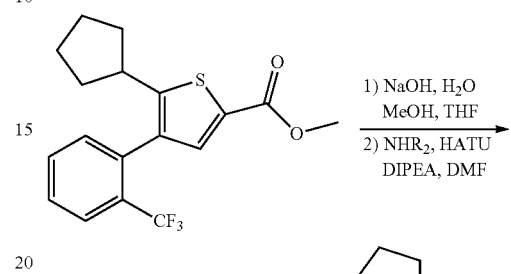
1) NaOH, H₂O
   MeOH, THF
2) NHR₂, HATU
   DIPEA, DMF
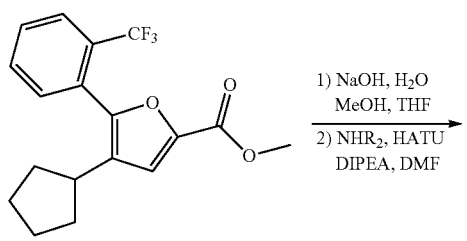
1) NaOH, H₂O
   MeOH, THF
2) NHR₂, HATU
   DIPEA, DMF
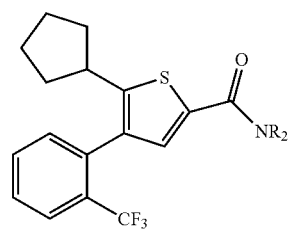
II
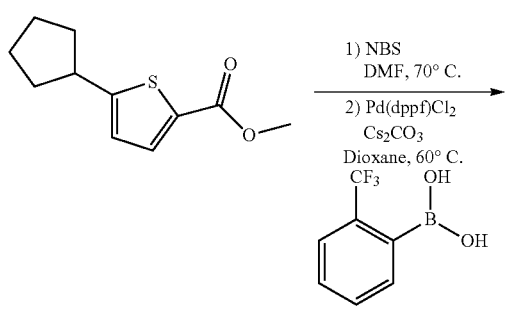
4.3.3. Thiophenes
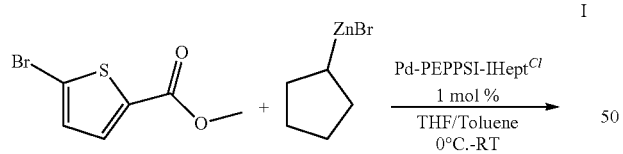
I
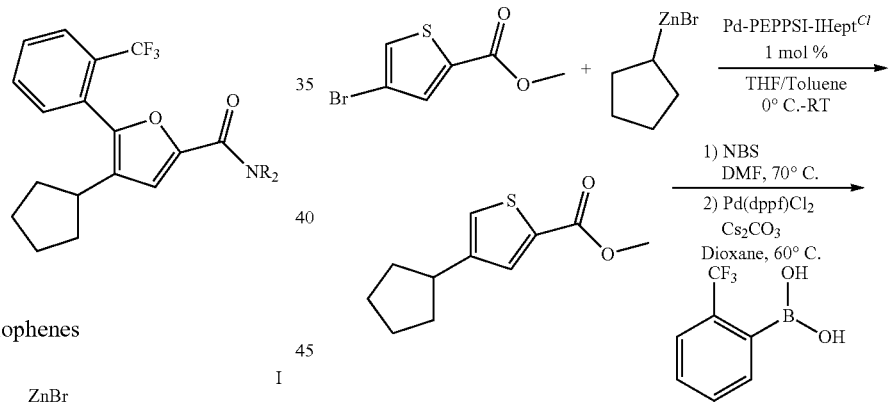
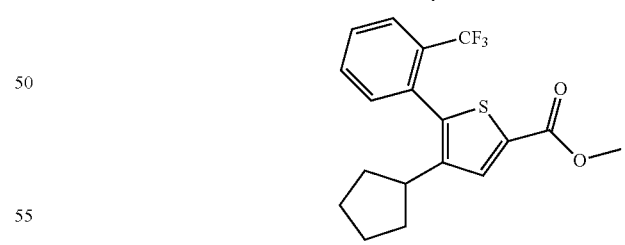
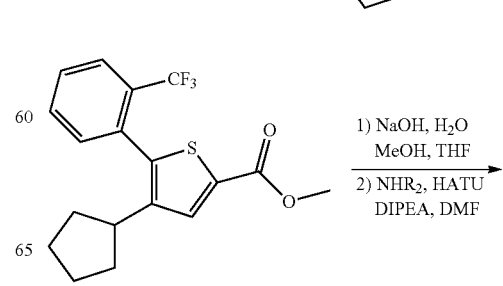
1) NaOH, H₂O
   MeOH, THF
2) NHR₂, HATU
   DIPEA, DMF

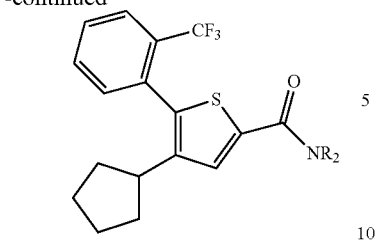
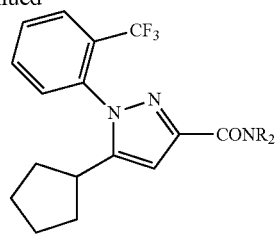
4.3.4. Pyrazoles
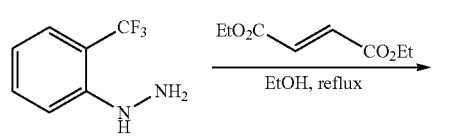
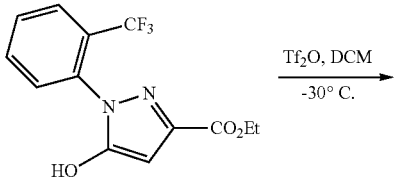
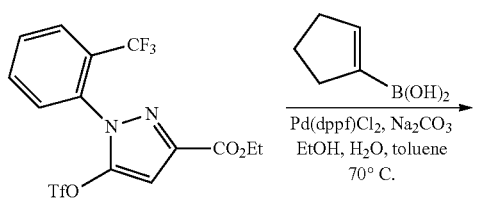
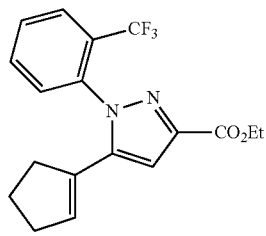
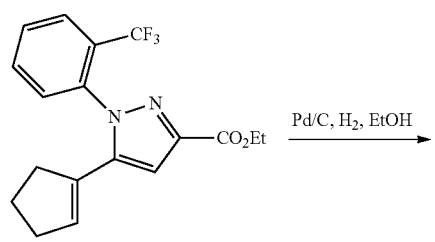
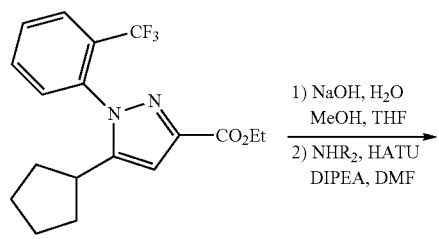
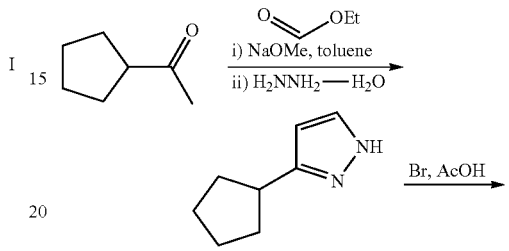
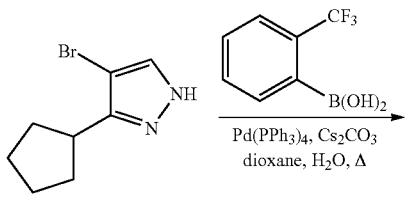
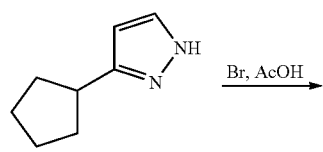
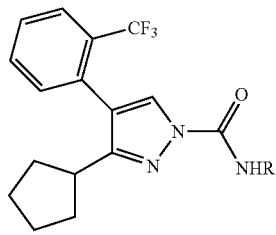
4.3.5. Imidazoles
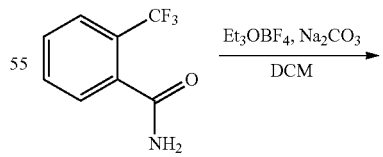
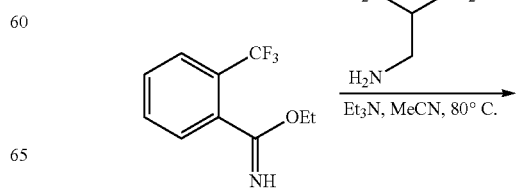

25
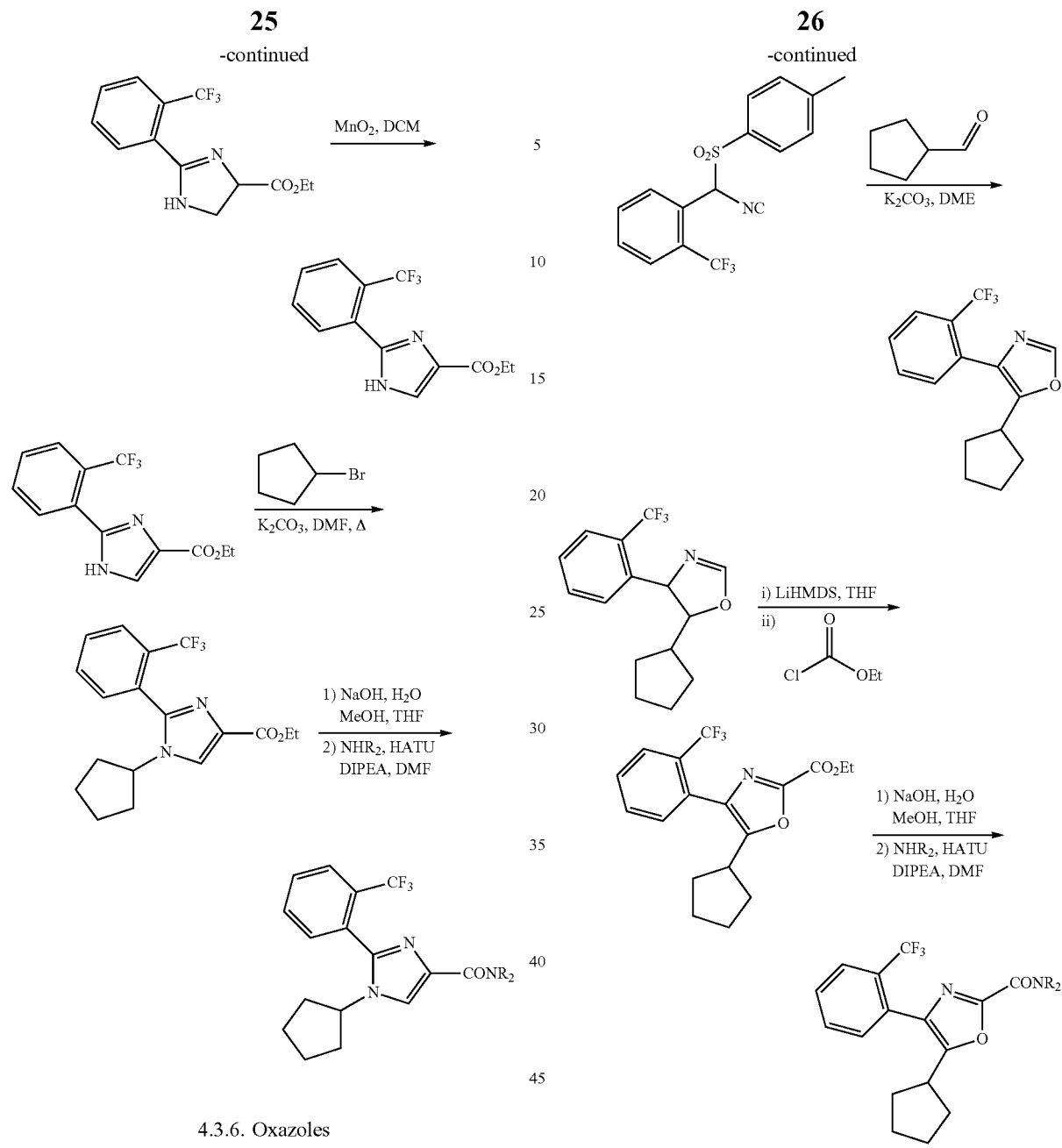
4.3.6. Oxazoles
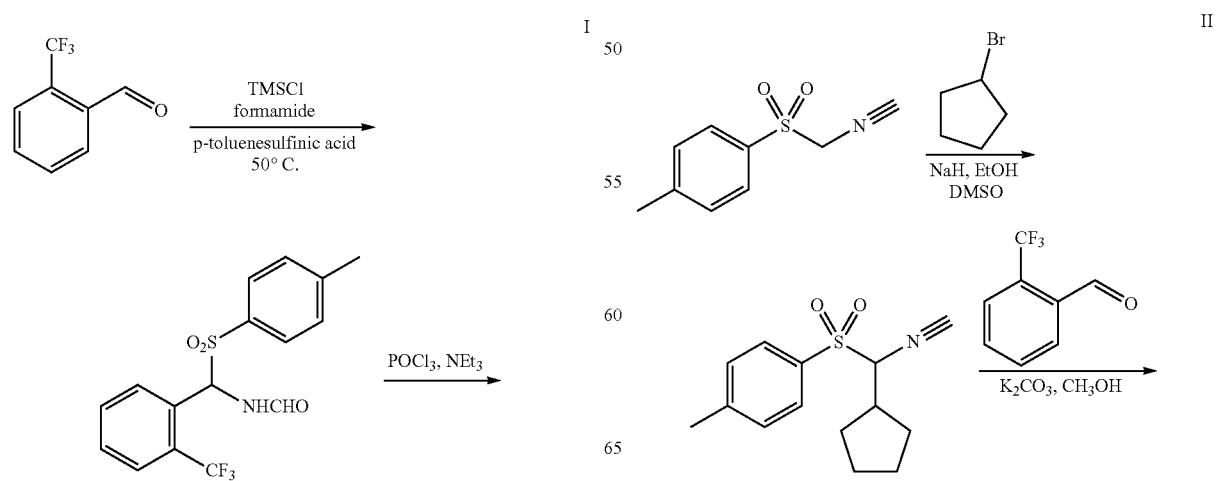

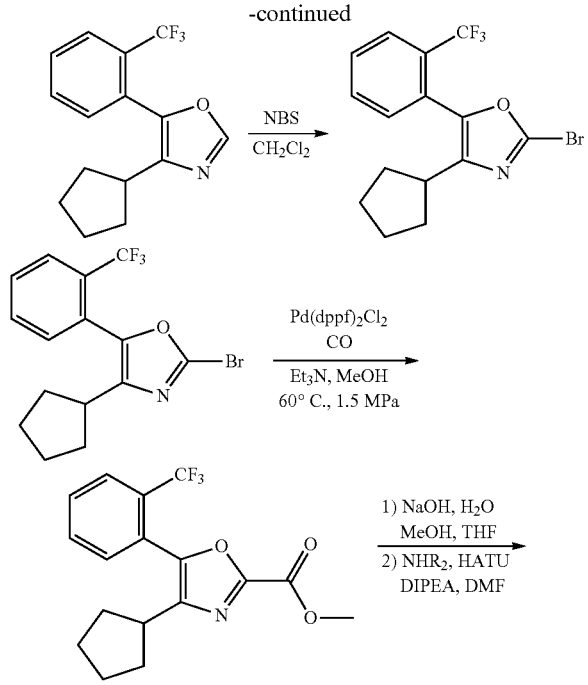
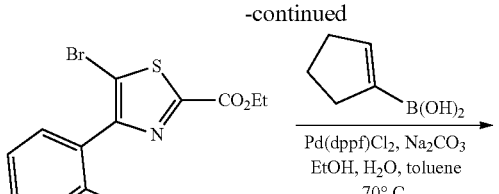
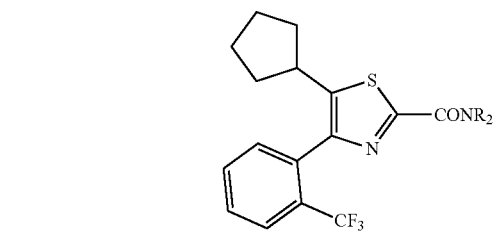
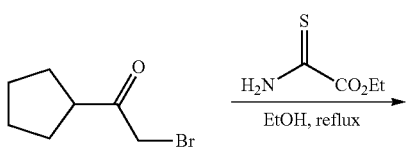
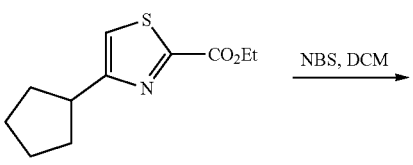
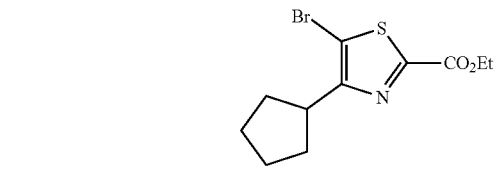
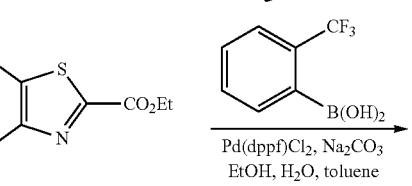
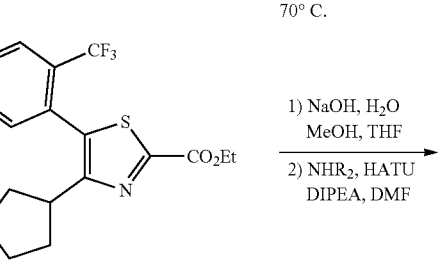
4.3.7. Thiazoles
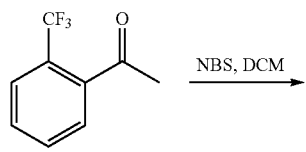
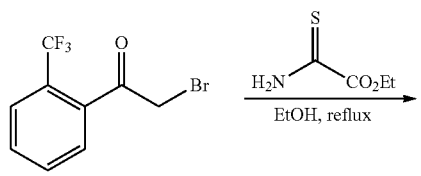
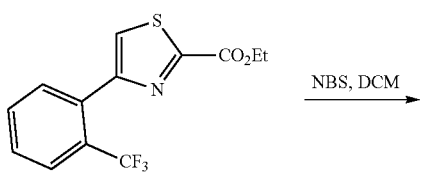
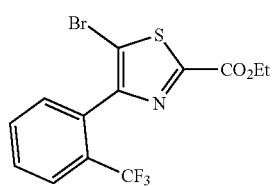

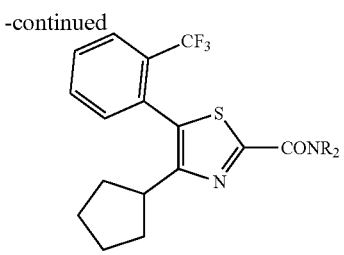

4.3.8. Triazoles

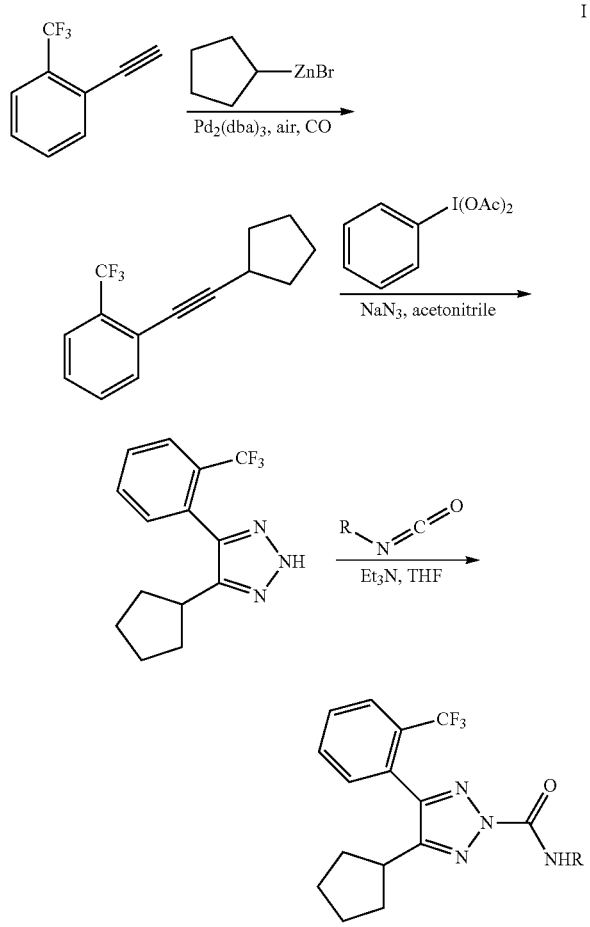

4.4. Pharmaceutical Compositions

The disclosure also provides pharmaceutical compositions comprising an effective amount of a compound Formula I (e.g., any of the formulae and/or structures disclosed herein), or a pharmaceutically acceptable salt of said compound; and a pharmaceutically acceptable carrier.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866 (Infeld et al.); and US Pat. Pubs. 20060094744 (Maryanoff et al.) and 20060079502 (Lang).

The pharmaceutical compositions of the disclosure include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, PA (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product. In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031 (Rabinowitz & Zaffaroni).

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene or polyoxypropylene compounds, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the therapeutics may be local, so as to be administered at the site of interest. Various techniques can be used for providing the compositions at the site of interest, such as injection, use of catheters, trocars, projectiles, pluronic gels, stents, sustained drug release polymers or other devices which provide for internal access. Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. No. 6,099,562 (Ding & Helmus); U.S. Pat. No. 5,886,026 (Hunter et al.); and U.S. Pat. No. 5,304,121 (Sahatjian). The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active. Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

In one embodiment, this disclosure provides a composition comprising a compound of Formula I, or more specific compounds disclosed herein, to treat or prevent asthma, atherosclerosis, cancer, cardiomyopathy, diabetes, dyslipidemia, HIV neurodegeneration, hypertension, inflammation, liver disease, metabolic disorder, neurodegenerative disease, obesity, or preeclampsia. In another embodiment, the disclosure provides a composition comprising a compound of Formula I, or more specific compounds disclosed herein, to treat or prevent cancer, cell proliferation, diabetes, fluid homeostasis, heart diseases (e.g., hypertension and heart failure, such as congestive heart failure), HIV infection, immune function, obesity, stem cell trafficking, metastatic cancer or a vein-related disorder such as an angioma, a venous insufficiency, a stasis, or a thrombosis.

In another embodiment, a composition of this disclosure further comprises a second therapeutic agent. In one embodiment, the second therapeutic agent is one or more additional compounds of the disclosure. In another embodiment, the second therapeutic agent may be selected from any compound or therapeutic agent known to have or that demonstrates advantageous properties when administered with a compound having the same mechanism of action as the APJ receptor compound of Formula I.

In a particular embodiment, the second therapeutic is an agent useful in the treatment or prevention of a disease or condition selected from acute decompensated heart failure (ADHF), amyotrophic lateral sclerosis, arrhythmia, asthma, atherosclerosis, atherosclerosis, atrial fibrillation, Brugada syndrome, burn injuries (including sunburn), cancer, cardiac fibrosis, cardiomyopathy, cerebrovascular accidents, chronic heart failure, diabetes (including gestational diabetes), dyslipidemia, HIV neurodegeneration, hypertension, inflammation, ischemic cardiovascular diseases, liver disease, metabolic disorder, neurodegenerative disease, obesity, peripheral arterial disease, preeclampsia, pulmonary hypertension, restenosis, transient ischemic attacks, traumatic brain injuries, ventricular tachycardia, or water retention. In another embodiment, the second therapeutic is an agent useful in the treatment or prevention of a disease or condition selected from cancer, cell proliferation, diabetes, fluid homeostasis, heart diseases (e.g., hypertension and heart failure, such as congestive heart failure), HIV infection, immune function, obesity, stem cell trafficking, or metastatic cancer.

For example, when the disease or condition is congestive heart failure, the second therapeutic agent can be selected from: ACE inhibitors, beta blockers, vasodilator, calcium channel blockers, loop diuretics, aldosterone antagonists, and angiotensin receptor blockers.

When the disease or condition being treated is hypertension, the second therapeutic agent can be selected from: α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

Non-limiting examples of α-Blockers include doxazosin, prazosin, tamsulosin, and terazosin.

Non-limiting examples of β-Blockers for combination therapy are selected from acebutolol, acetutolol, atenolol, bisoprol, bupranolol, carteolol, carvedilol, celiprolol, esmolol, mepindolol, metoprolol, nadolol, oxprenolol, penbutolol, pindolol, propanolol, taliprolol, and their pharmaceutically acceptable salts.

Non-limiting examples of calcium channel blockers include dihydropyridines (DHPs) and non-DHPs. The preferred DHPs are selected from the group consisting of amlodipine, felodipine, isradipine, lacidipine, nicardipine, nifedipine, nigulpidine, niludipine, nimodiphine, nisoldipine, nitrendipine, nivaldipine, ryosidine, and their pharmaceutically acceptable salts. Non-DHPs are selected from anipamil, diltiazem, fendiline, flunarizine, gallopamil, mibefradil, prenylamine, tiapamil, and verampimil and their pharmaceutically acceptable salts.

A diuretic is, for example, a thiazide derivative selected from amiloride, chlorothalidon, chlorothiazide, hydrochlorothiazide, and methylchlorothiazide.

Non-limiting examples of centrally acting antiphypertensives include clonidine, guanabenz, guanfacine and methyldopa.

Non-limiting examples of ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Non-limiting examples of dual ACE/NEP inhibitors are, for example, omapatrilat, fasidotril, and fasidotrilat.

Non-limiting examples of preferred ARBs include candesartan, eprosartan, irbesartan, losartan, olmesartan, tasosartan, telmisartan, and valsartan.

Non-limiting examples of preferred aldosterone synthase inhibitors are anastrozole, fadrozole, and exemestane.

Non-limiting examples of preferred aldosterone-receptor antagonists are spironolactone and eplerenone.

Non-limiting examples of preferred endothelin antagonist is, for example, bosentan, enrasentan, atrasentan, darusentan, sitaxentan, and tezosentan and their pharmaceutically acceptable salts.

In one embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970, 537.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

The compounds for use in the method of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily treatment dose or one of multiple daily treatment doses (e.g., about 1 to 4 or more times per day). When multiple daily treatment doses are used, the unit dosage form can be the same or different for each dose.

4.5. Methods of Treatment

The disclosure also includes methods of treating diseases, disorders or pathological conditions which benefit from modulation of the APJ receptor comprising administering an effective amount of an APJ receptor compound of the disclosure to a subject in need thereof. Diseases and conditions which can benefit from modulation (inhibition or activation) of the APJ receptor include, but are not limited to, acute decompensated heart failure (ADHF), amyotrophic lateral sclerosis, arrhythmia, asthma, atherosclerosis, atherosclerosis, atrial fibrillation, Brugada syndrome, burn injuries (including sunburn), cancer, cardiac fibrosis, cardiomyopathy, cerebrovascular accidents, chronic heart failure, diabetes (including gestational diabetes), dyslipidemia, HIV neurodegeneration, hypertension, inflammation, ischemic cardiovascular diseases, liver disease, metabolic disorder, neurodegenerative disease, obesity, peripheral arterial disease, preeclampsia, pulmonary hypertension, restenosis, transient ischemic attacks, traumatic brain injuries, ventricular tachycardia, or water retention. More specifically, the hypertension may be pulmonary arterial hypertension. The liver disease may be alcoholic liver disease, toxicant-induced liver disease or viral-induced liver disease and the renal dysfunction may be polycystic kidney disease. The apelin receptor system is involved in vein-related disorders. See, e.g., Lathen et al., "ERG-APLNR Axis Controls Pulmonary Venule Endothelial Proliferation in Pulmonary Veno-Occlusive Disease" 2014 Circulation 130: 1179-1191. Apelin receptor system has also been implicated in heart failure. See, e.g., Sheikh et al., "In vivo genetic profiling and cellular localization of apelin reveals a hypoxia-sensitive, endothelial-centered pathway activated in ischemic heart failure" 2007 Am J Physiol Heart Circ Physiol 294: H88-H98. The contents of both Lathen et al. and Sheikh et al. are hereby incorporated by reference in their entireties into the present disclosure.

In one non-limiting embodiment, the disclosure provides a method of treating an apelin receptor (APJ) related disorder in a subject which comprises administering to the subject the compound of embodiment 1. The apelin receptor (APJ) related disorder may be asthma, atherosclerosis, cancer, cardiomyopathy, diabetes, dyslipidemia, hypertension, inflammation, liver disease, metabolic disorder, neurodegenerative disease, obesity, or preeclampsia. The disclosure provides methods further comprising treating the subject with an α-blocker, an angiotensin converting enzyme (ACE) inhibitor, an angiotensin-receptor blocker (ARB), a β-blocker, a calcium channel blocker, or a diuretic. Alternatively, the disclosure provides a method to treat or prevent a vein-related disorder such as an angioma, a venous insufficiency, a stasis or a thrombosis.

In addition, the disclosure provides a method of preventing HIV neurodegeneration in a subject which comprises administering to the subject the compound of embodiment 1.

In one embodiment, an effective amount of a compound of this disclosure can range from about 0.005 mg to about 5000 mg per treatment. In more specific embodiments, the range is from about 0.05 mg to about 1000 mg, or from about 0.5 mg to about 500 mg, or from about 5 mg to about 50 mg. Treatment can be administered one or more times per day (for example, once per day, twice per day, three times per day, four times per day, five times per day, etc.). When multiple treatments are used, the amount can be the same or different. It is understood that a treatment can be administered every day, every other day, every 2 days, every 3 days, every 4 days, every 5 days, etc. For example, with every other day administration, a treatment dose can be initiated on Monday with a first subsequent treatment administered on Wednesday, a second subsequent treatment administered on Friday, etc. Treatment is typically administered from one to two times daily. Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Alternatively, the effective amount of a compound of the disclosure is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

In another embodiment, any of the above methods of treatment comprises the further step of co-administering to said subject one or more second therapeutic agents. The choice of second therapeutic agent may be made from any second therapeutic agent known to be useful for co-administration with a compound that modulates the APJ receptor. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

The term "co-administered" as used herein means that the second therapeutic agent may be administered together with a compound of this disclosure as part of a single dosage form (such as a composition of this disclosure comprising a compound of the disclosure and a second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a subject does not preclude the separate administration of that same therapeutic agent, any other second therapeutic agent or any compound of this disclosure to said subject at another time during a course of treatment.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

4.6. Kits

The present disclosure also provides kits for use to treat the target disease, disorder or condition. These kits comprise (a) a pharmaceutical composition comprising a compound of Formula I, or a salt thereof, wherein said pharmaceutical composition is in a container; and (b) instructions describing a method of using the pharmaceutical composition to treat the target disease, disorder or condition.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this disclosure may also comprise a device to administer or to measure out a unit dose of the pharmaceutical composition. Such a device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiments, the kits of this disclosure may comprise in a separate vessel of container a pharmaceutical composition comprising a second therapeutic agent, such as one of those listed above for use for co-administration with a compound of this disclosure.

Unless defined otherwise, all technical and scientific terms used herein have the same meaning as commonly understood by one of ordinary skill in the art to which this disclosure belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

The following Examples further illustrate the disclosure and are not intended to limit the scope of the disclosure. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

5. EXAMPLES

5.1. Method and Preparation of a Representative Compounds

Scheme 1: Preparation of (S)-3-(5-cyclopentyl-1-(2-(trifluoromethyl)pyridin-3-yl)-1H-1,2,4-triazol-3-carboxamido)-5-(3,3-difluoropiperidin-1-yl)pentanoic acid

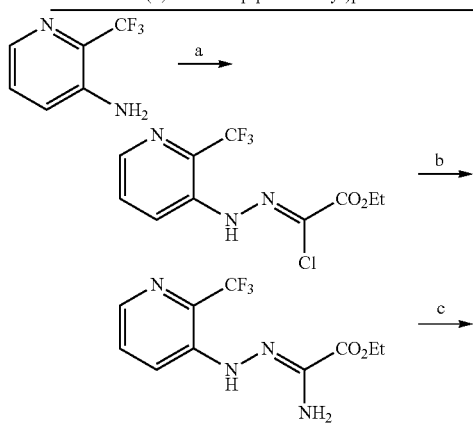

-continued

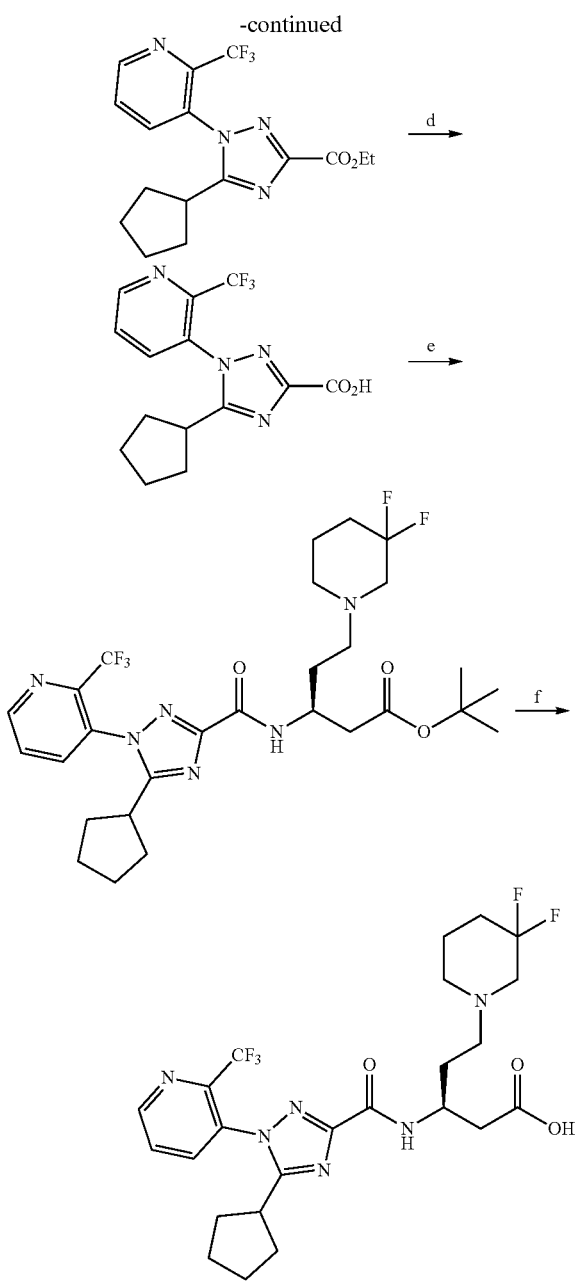

Reagents and conditions: (a) 6N aqs. HCl, NaNO₂, EtOH, 0° C., ethyl-2-chloroacetoacetate, 1 h; (b) 0.5M NH₃ in dioxane, 0° C. to rt, 18 h; (c) cyclopentanecarbonyl chloride, toluene, 0 –110° C. for 3 days; (d) 1N NaOH, THF:MeOH (1:1), rt, 18 h; (e) (S)-tert-butyl 3-amino-5-(3,3-difluoropiperidin-1-yl)pentanoate, HATU, i-PrNEt2, DMF, 0° C. to rt, 18 h; (f) 4M HCl in dioxane, rt, 18 h

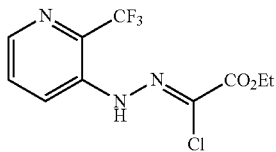 [SMILES: CCOC(=O)/C(Cl)=N/Nc1cccnc1C(F)(F)F]

(Z)-ethyl 2-chloro-2-(2-(2-(trifluoromethyl)pyridin-3-yl)hydrazono)acetate: A 6N aqueous solution of HCl (5.9 mL) was added to 2-(trifluoromethyl)pyridin-3-amine (1.00 g, 6.17 mmol, 1.00 equiv.) at rt. The reaction mixture was cooled at 0° C. and a solution of sodium nitrite (426 mg, 6.17 mmol, 1.00 equiv.) in water (1.2 mL) was added dropwise. The reaction mixture was stirred at 0° C. for 30 min. At the same temperature, a solution of ethyl-2-chloroacetoacetate (1.02 g, 6.21 mmol, 1.00 equiv.) in ethanol (2.3 mL) was added during 1 h using a push syringe. The reaction mixture was stirred at 0° C. for 30 min and a solution of sodium acetate (1.52 g, 18.5 mmol, 3.00 equiv.) in water (4.7 mL) was added. The reaction mixture was stirred at rt for 18 h. The pale orange precipitate was filtered, washed with water and dried under vacuum to provide 1.39 g (76%) of the title compound as an orange solid. m/z (M+H)⁺=296.0; $R_T$=1.73 min; purity=98.2%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.30 (t, J=7.1 Hz, 3H), 4.32 (q, J=7.1 Hz, 2H), 7.76 (dd, J=8.5, 4.5 Hz, 1H), 8.04 (d, J=8.5 Hz, 1H), 8.46 (dd, J=4.4, 0.8 Hz, 1H), 9.52 (s, 1H).

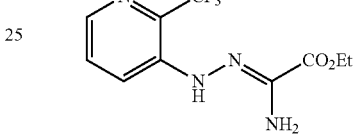

(Z)-ethyl 2-amino-2-(2-(2-(trifluoromethyl)pyridin-3-yl)hydrazono)acetate: A solution of (Z)-ethyl 2-chloro-2-(2-(2-(trifluoromethyl)pyridin-3-yl)hydrazono)acetate (1.39 g, 4.70 mmol, 1.00 equiv.) in THF (3 mL) was added to a 0.5M solution of ammonia in dioxane (28.2 mL, 14.1 mmol, 3.00 equiv.) at 0° C. The reaction mixture was stirred for 18 h. The solvent was evaporated under reduced pressure and chloroform (50 mL) was added. The insoluble ammonium chloride was filtered and the filtrate was evaporated to provide 1.30 g (quant. yield) of the title compound as a viscous orange oil. m/z (M+H)⁺=277.0; RT=1.34 min; purity=99%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.28 (t, J=7.1 Hz, 3H), 4.25 (q, J=7.1 Hz, 2H), 6.56 (s, 2H), 7.57 (dd, J=8.6, 4.3 Hz, 1H), 8.02 (dd, J=8.6, 0.9 Hz, 1H), 8.05 (s, 1H), 8.10 (dd, J=4.4, 1.2 Hz, 1H).

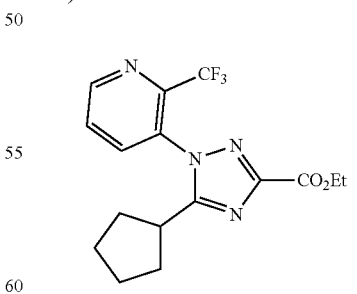

Ethyl 5-cyclopentyl-1-(2-(trifluoromethyl)pyridin-3-yl)-1H-1,2, 4-triazole-3-carboxylate A solution of cyclopentanecarbonyl chloride (96 mg, 0.73 mmol, 2.5 equiv.) in toluene (0.15 mL) was added to a solution of (Z)-ethyl 2-amino-2-(2-(2-(trifluoromethyl)pyridin-3-yl)hydrazono)acetate (100 mg, 0.362 mmol, 1.00 equiv.) in toluene (0.20 mL) at 0° C. The reaction mixture was stirred at rt for 1.5 h and another portion of cyclopentanecarbonyl chloride (72 mg, 0.54 mmol, 1.5 equiv.) was added. The reaction mixture was heated at 110° C. for 3 days. The solvent was evaporated and the crude product was purified by flash chromatography on silica gel column using a solution of ethyl acetate in hexanes (10 to 60%) to provide 83 mg (65%) of the title compound as a pale orange solid. m/z (M+H)$^+$=355.2; R$_T$=1.62 min; purity=86%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.31 (t, J=7.1 Hz, 3H), 1.58-1.47 (m, 2H), 1.88-1.69 (m, 6H), 2.92 (quint, J=7.9 Hz, 1H), 4.35 (q, J=7.1 Hz, 2H), 8.05 (dd, J=8.1, 4.7 Hz, 1H), 8.43 (d, J=8.1 Hz, 1H), 9.03 (d, J=4.7 Hz, 1H).

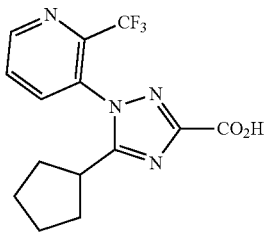 [SMILES: O=C(O)c1nc(C2CCCC2)n(-c2cccnc2C(F)(F)F)n1]

5-cyclopentyl-1-(2-(trifluoromethyl)pyridin-3-yl)-1H-1,2,4-triazole-3-carboxylic acid: A 1N solution of sodium hydroxide (0.47 mL, 0.47 mmol, 2.0 equiv.) was added to a solution of ethyl 5-cyclopentyl-1-(2-(trifluoromethyl)pyridin-3-yl)-1H-1,2,4-triazole-3-carboxylate (83 mg, 0.23 mmol, 1.00 equiv.) in THF:MeOH (1:1, 1.2 mL). The reaction mixture was stirred at rt for 18 h. 1H HCl was added until pH=1 and the mixture was extracted 2× with ethyl acetate. The combined organic layers were dried with sodium sulfate, filtered and evaporated to provide 61 mg (80%) of the title compound as a pale brown solid. m/z (M+H)$^+$=327.1; RT=1.13 min; purity=>99%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

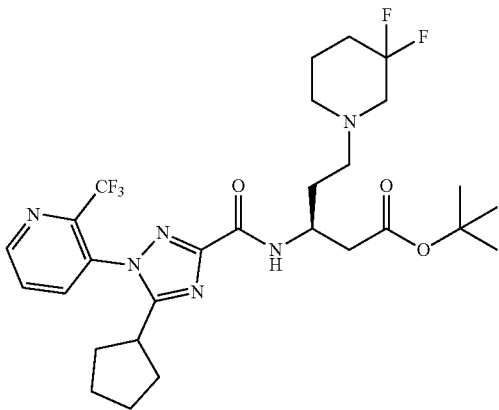 [SMILES: CC(C)(C)OC(=O)C[C@H](CCN1CCCC(F)(F)C1)NC(=O)c1nc(C2CCCC2)n(-c2cccnc2C(F)(F)F)n1]

(S)-tert-butyl 3-(5-cyclopentyl-1-(2-(trifluoromethyl) pyridin-3-yl)-1H-1,2,4-triazole-3-carboxamido)-5-(3,3-difluoropiperidin-1-yl)pentanoate: HATU (39 mg, 0.10 mmol, 1.1 equiv.) was added to a solution of (S)-tert-butyl 3-amino-5-(3,3-difluoropiperidin-1-yl)pentanoate (27 mg, 0.092 mmol, 1.0 equiv.), 5-cyclopentyl-1-(2-(trifluoromethyl)pyridin-3-yl)-1H-1,2,4-triazole-3-carboxylic acid (30 mg, 0.092 mmol, 1.0 equiv.) and diisopropylethylamine (48 μL, 0.28 mmol, 3.0 equiv.) in DMF (0.37 mL) at 0° C. The reaction mixture was stirred at rt for 18 h. Water was added followed by ethyl acetate. The phases were separated and the organic layer was washed with an aqueous saturated solution of sodium bicarbonate (3×), dried with sodium sulfate, filtered and evaporated. The crude product was purified by flash chromatography on silica gel using a solution of MeOH in DCM (0 to 5%) to provide 48.7 mg (88%) of the title compound as a pale orange oil. The compound was further purified by reverse chromatography on C-18 column using a solution of MeCN in water (containing 10 mM of ammonium formate, pH=3.8) (10 to 70%). Fractions were combined and evaporated. The residue was mixed with ethyl acetate and saturated aqueous NaHCO$_3$. The phases were separated and the organic layer was dried with sodium sulfate, filtered and evaporated to provide 28.6 mg (52%) as a pale yellow oil. m/z (M+H)$^+$=601.3; R$_T$=1.72 min; purity=>95%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

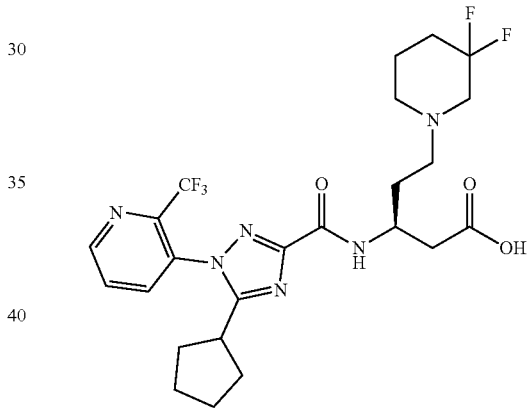

(S)-3-(5-cyclopentyl-1-(2-(trifluoromethyl)pyridin-3-yl)-1H-1,2,4-triazole-3-carboxamido)-5-(3,3-difluoropiperidin-1-yl)pentanoic acid: 4M HCl in dioxane (0.24 mL, 0.95 mmol, 20 equiv.) was added to (S)-tert-butyl 3-(5-cyclopentyl-1-(2-(trifluoromethyl)pyridin-3-yl)-1H-1,2,4-triazole-3-carboxamido)-5-(3,3-difluoropiperidin-1-yl)pentanoate (29 mg, 0.048 mmol, 1.0 equiv.). The reaction mixture was stirred at rt for 18 h and the solvent was evaporated. The crude product was purified by reverse chromatography on C-18 column using a solution of MeCN in water (containing 10 mM of ammonium bicarbonate, pH=10) (5 to 50%, 205 nM detection). Pure fractions were lyophilized to provide 15.8 mg (61%) of the title compound as a white solid. m/z (M+H)$^+$=545.2; R$_T$=1.25 min; purity=99.5%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.58-1.48 (m, 2H), 1.68-1.59 (m, 2H), 1.88-1.69 (m, 10H), 2.45-2.30 (m, 4H), 2.52-2.46 (m, 1H), 2.66-2.53 (m, 3H), 2.89 (quint, J=8.1 Hz, 1H), 4.35-4.26 (m, 1H), 8.04 (dd, J=8.2, 4.7 Hz, 1H), 8.41 (d, J=8.2 Hz, 1H), 8.48 (s, 1H), 9.02 (d, J=4.7 Hz, 1H).

Scheme 2: Preparation of (S)-3-(1-cyclopentyl-5-(3-(trifluoromethyl)pyridin-2-yl)-1H-1,2,4-triazole-3-carboxamido)-5-(3,3-difluoropiperidin-1-yl)pentanoic acid

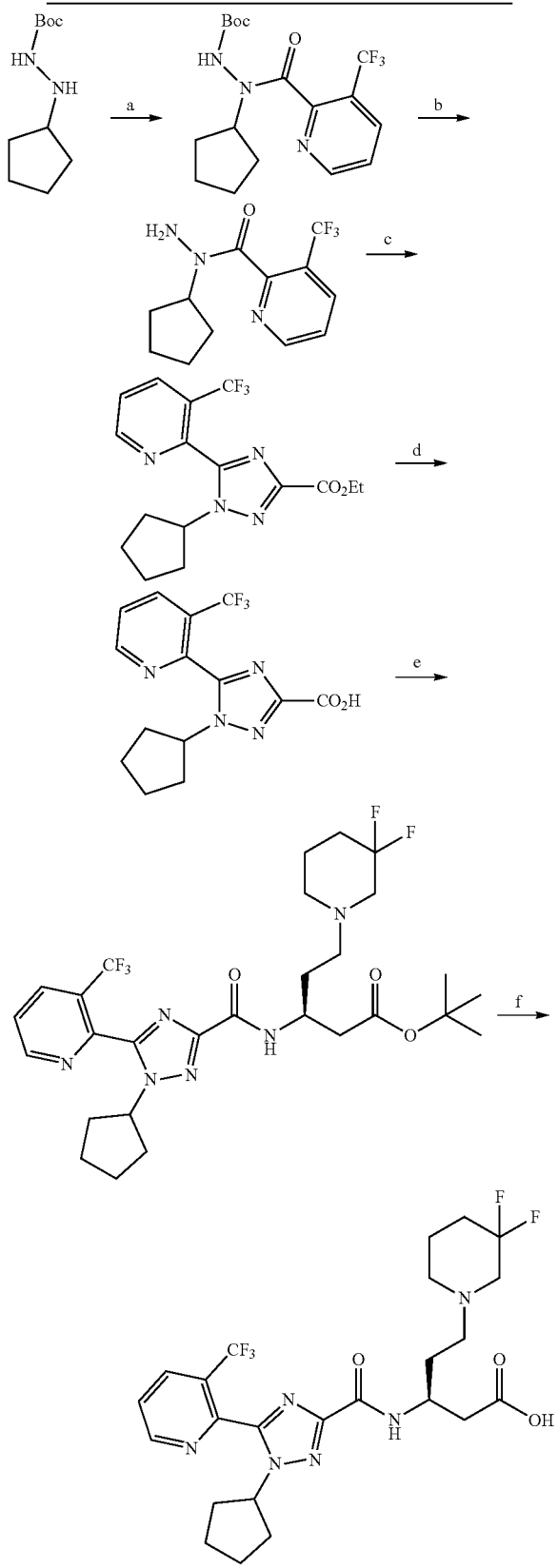

Reagents and conditions: (a) 3-(trifluoromethyl)picolinic acid, HATU, i-PrNEt2, DMF, 0° C. to rt, 18 h; (b) 4M HCl in dioxane, rt, 18 h; (c) Ethyl 2-amino-2-thioxoacetate, toluene, CH₃COOH, 110° C., 3 days; (d) NaOH, THF:MeOH (1:1), rt, 18 h; (e) (S)-tert-butyl 3-amino-5-(3,3-difluoropiperidin-1-yl)pentanoate, HATU, HOAt, i-PrNEt2, DMF, 0° C. to rt, 18 h; (f) 4M HCl in dioxane, rt, 18 h

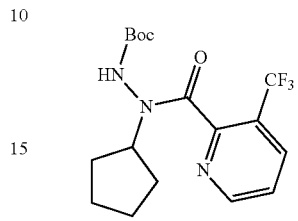

Tert-butyl 2-cyclopentyl-2-(3-(trifluoromethyl)picolinoyl)hydrazinecarboxylate: HATU (4.18 g, 11.0 mmol, 1.10 equiv.) was added to a solution of tert-butyl 2-cyclopentylhydrazinecarboxylate (2.00 g, 10.0 mmol, 1.00 equiv.), 3-(trifluoromethyl)picolinic acid (2.10 g, 11.0 mmol, 1.10 equiv.) and diisopropylethylamine (5.22 mL, 30.0 mmol, 3.00 equiv.) in DMF (40 mL) at 0° C. The reaction mixture was stirred at rt for 18 h. The mixture was dissolved in EtOAc and the solution was washed with brine (4×), dried with sodium sulfate, filtered and evaporated. The crude product was purified by flash chromatography on silica gel using a solution of ethyl acetate in hexanes (20 to 60%) to provide 2.94 g (74%) of the title compound as a white solid. m/z (M+H)⁺=374.2; RT=1.67 min; purity=98.7%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

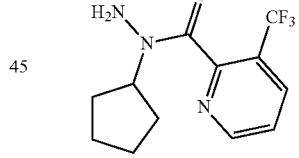

N-cyclopentyl-3-(trifluoromethyl)picolinohydrazide: 4M HCl in dioxane (20 mL, 79 mmol, 10 equiv.) was added to tert-butyl 2-cyclopentyl-2-(3-trifluoromethyl)picolinoyl)hydrazinecarboxylate (2.94 g, 7.87 mmol, 1.00 equiv.). The reaction was stirred at rt for 18 h. A saturated aqueous solution of NaHCO₃ (100 mL) was slowly added, followed by 6N NaOH until pH=10. The mixture was extracted 4× with a solution of THF in DCM (1:3), the combined organic layers were dried with sodium sulfate, filtered and evaporated to provide 2.19 g (quantitative yield) of the title compound as a pale yellow oil. m/z (M+H)⁺=274.1; $R_T$=1.25-1.35 min (the signal is broad with two peaks); purity=92.6%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

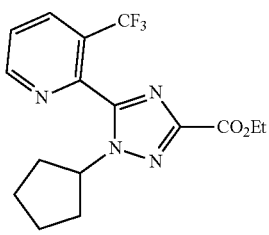

Ethyl 1-cyclopentyl-5-(3-(trifluoromethyl)pyridin-2-yl)-1H-1,2,4-triazole-3-carboxylate: Ethyl 2-amino-2-thioxoacetate (586 mg, 4.39 mmol, 3.00 equiv.) was added to a solution of N-cyclopentyl-3-(trifluoromethyl)picolinohydrazide (400 mg, 1.46 mmol, 1.00 equiv.) in toluene (2.4 mL). Acetic acid (0.24 mL) was added and the reaction mixture was heated at 110° C. for 3 days. The solvent was evaporated and the crude product was purified by flash chromatography on silica gel using a solution of ethyl acetate in hexanes (30 to 50%) to provide 216 mg (42%) of the title compound as a brown oil. m/z (M+H)$^+$=355.2; R$_T$=1.68 min; purity=86%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.32 (t, J=7.1 Hz, 3H), 1.62-1.50 (m, 2H), 1.95-1.78 (m, 4H), 2.05-1.96 (m, 2H), 4.36 (q, J=7.1 Hz, 2H), 4.71-4.63 (m, 1H), 7.92 (ddd, J=8.1, 4.9, 0.7 Hz, 1H), 8.50 (dd, J=8.2, 1.2 Hz, 1H), 9.06 (dd, J=4.8, 0.9 Hz, 1H).

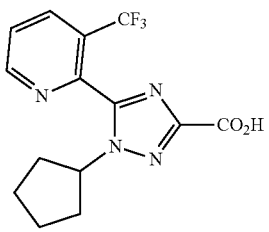 [SMILES: O=C(O)c1nc(-c2ncccc2C(F)(F)F)n(C2CCCC2)n1]

1-Cyclopentyl-5-(3-(trifluoromethyl)pyridin-2-yl)-1H-1,2,4-triazole-3-carboxylic acid: 1N NaOH (1.2 mL, 1.2 mmol, 2.0 equiv.) was added to a solution of ethyl 1-cyclopentyl-5-(3-(trifluoromethyl)pyridin-2-yl)-1H-1,2,4-triazole-3-carboxylate in THF:MeOH (1:1, 3.1 mL). The reaction mixture was stirred at rt for 18 h. 1H HCl was added to acidify the mixture. The mixture was stirred for 2 min and a precipitate formed, then filtered and dried under vacuum to provide 86 mg (43%) of the title compound as a beige solid. m/z (M+H)$^+$=327.1; R$_T$=1.13 min; purity=98.5%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

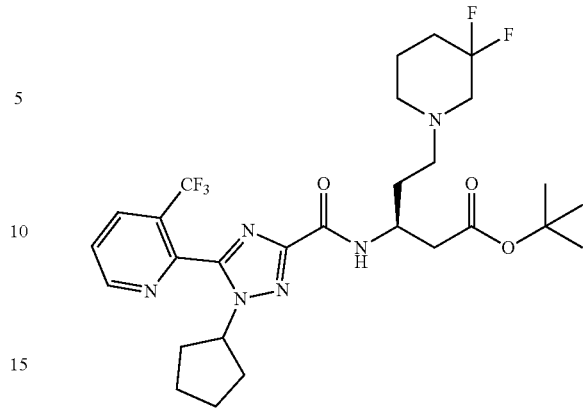

(S)-tert-butyl 3-(1-cyclopentyl-5-(3-(trifluoromethyl)pyridin-2-yl)-1H-1,2,4-triazole-3-carboxamido)-5-(3,3-difluoropiperidin-1-yl)pentanoate: HATU (39 mg, 0.10 mmol, 1.1 equiv.) was added to a solution of (S)-tert-butyl 3-amino-5-(3,3-difluoropiperidin-1-yl)pentanoate (27 mg, 0.092 mmol, 1.0 equiv.), 1-cyclopentyl-5-(3-(trifluoromethyl)pyridin-2-yl)-1H-1,2,4-triazole-3-carboxylic acid (30 mg, 0.092 mmol, 1.0 equiv.) and diisopropylethylamine (48 μL, 0.28 mmol, 3.0 equiv.) in DMF (0.37 mL) at 0° C. The reaction mixture was stirred at rt for 18 h. Water was added followed by ethyl acetate. The phases were separated and the organic layer was washed with an aqueous saturated solution of sodium bicarbonate (3×), dried with sodium sulfate, filtered and evaporated. The crude product was purified by flash chromatography on silica gel using a solution of MeOH in DCM (0 to 10%) to provide 35.5 mg (64%) of the title compound as a pale orange oil. m/z (M+H)$^+$=601.3; R$_T$=1.74 min; purity=96.8%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, CDCl$_3$) δ 1.43 (s, 9H), 1.79-1.70 (m, 2H), 1.63-1.53 (m, 2H), 1.91-1.80 (m, 4H), 2.04-1.92 (m, 4H), 2.23-2.12 (m, 2H), 2.48-2.40 (m, 2H), 2.68-2.50 (m, 6H), 4.52-4.45 (m, 1H), 4.56 (quint, J=7.6 Hz, 1H), 7.65-7.59 (m, 1H), 7.75 (d, J=9.1 Hz, 1H), 8.19 (dd, J=8.1, 1.3 Hz, 1H), 8.93 (dd, J=4.8, 1.1 Hz, 1H).

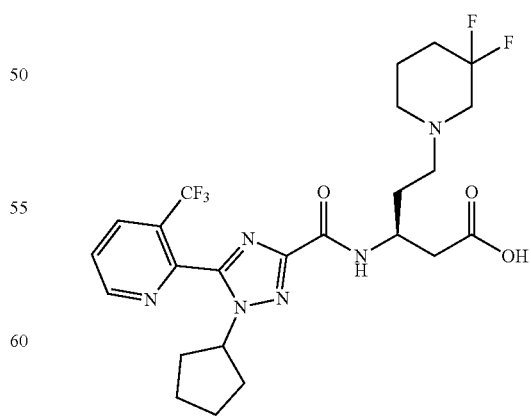

(S)-3-(1-cyclopentyl-5-(3-(trifluoromethyl)pyridin-2-yl)-1H-1,2,4-triazole-3-carboxamido)-5-(3,3-difluoropiperidin-1-yl)pentanoic acid: 4M HCl in dioxane (0.30 mL, 1.2 mmol, 20 equiv.) was added to (S)-tert-butyl 3-(1-cyclopentyl-5-(3-(trifluoromethyl)pyridin-2-yl)-1H-1,2,4-triazole-3-carboxamido)-5-(3,3-difluoropiperidin-1-yl)pentanoate (36 mg, 0.059 mmol, 1.0 equiv.). The reaction mixture was stirred at rt for 3 h and the solvent was evaporated. The crude product was purified by reverse chromatography on C-18 column using a solution of MeCN in water (containing 10 mM of ammonium bicarbonate, pH=10) (5 to 50%, 205 nM detection). Pure fractions were lyophilized to provide 17.3 mg (54%) of the title compound as a white solid. m/z (M+H)$^+$=545.3; RT=1.28 min; purity=>99%. HPLC conditions: Column: XBridge C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.66-1.53 (m, 4H), 1.77-1.68 (m, 2H), 2.03-1.77 (m, 8H), 2.44-2.31 (m, 4H), 2.54-2.44 9 m, 2H), 2.63-2.55 (m, 2H), 4.34-4.24 (m, 1H), 4.60 (quint, J=7.0 Hz, 1H), 7.91 (dd, J=7.8, 5.1 Hz, 1H), 8.46 (s, 1H), 8.51 (d, J=7.8 Hz, 1H), 9.06 (d, J=3.9 Hz, 1H).

Scheme 3: Preparation of (S)-N-(1-(cyclobutylamino)-5-(3,3-difluoropiperidin-1-yl)-1-oxopentan-3-yl)-2-cyclopentyl-1-(2-(trifluoromethyl)phenyl)-1H-imidazole-4-carboxamide

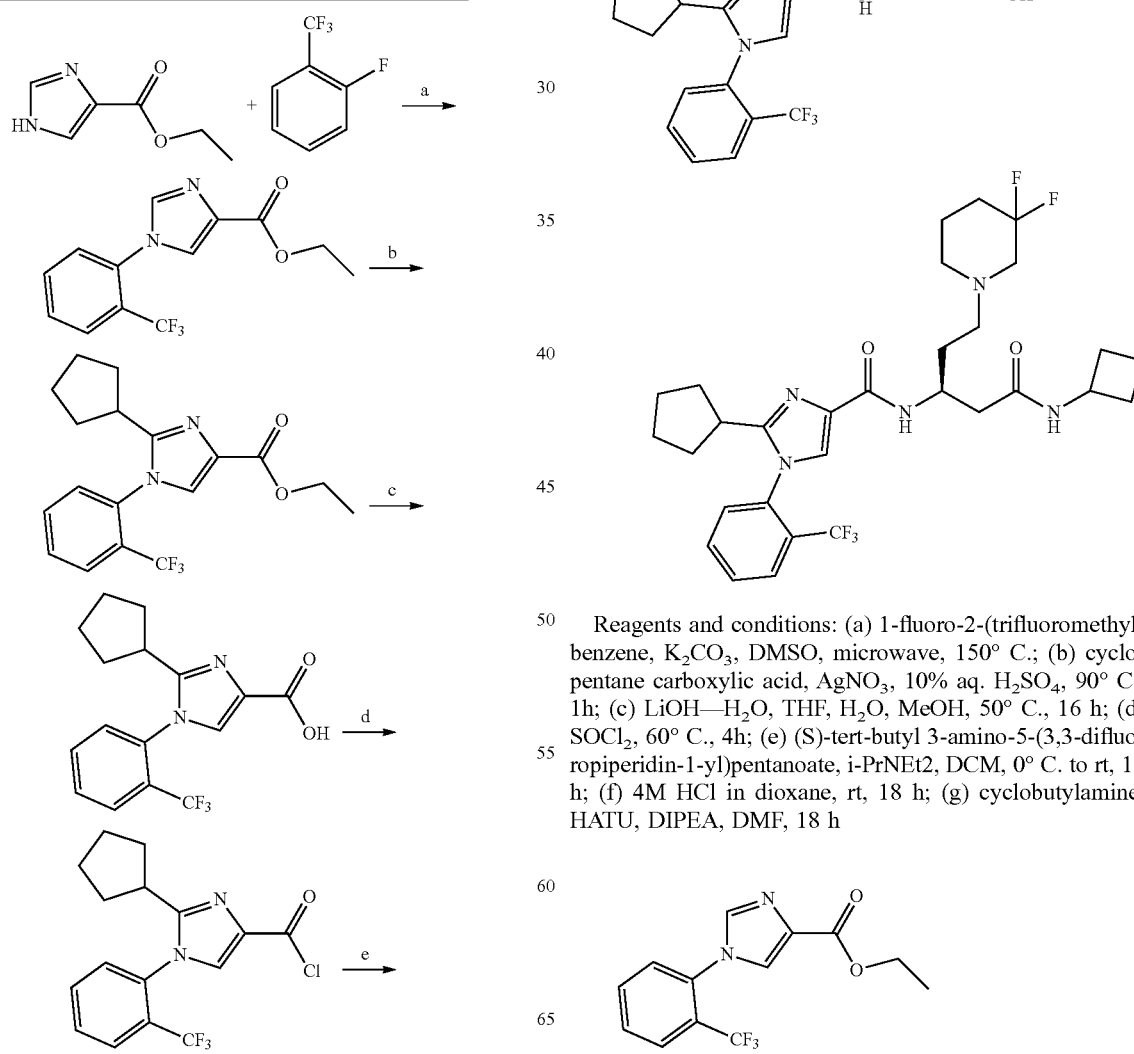

Reagents and conditions: (a) 1-fluoro-2-(trifluoromethyl)benzene, K$_2$CO$_3$, DMSO, microwave, 150° C.; (b) cyclopentane carboxylic acid, AgNO$_3$, 10% aq. H$_2$SO$_4$, 90° C., 1h; (c) LiOH—H$_2$O, THF, H$_2$O, MeOH, 50° C., 16 h; (d) SOCl$_2$, 60° C., 4h; (e) (S)-tert-butyl 3-amino-5-(3,3-difluoropiperidin-1-yl)pentanoate, i-PrNEt2, DCM, 0° C. to rt, 18 h; (f) 4M HCl in dioxane, rt, 18 h; (g) cyclobutylamine, HATU, DIPEA, DMF, 18 h Ethyl 1-(2-(trifluoromethyl)phenyl)-1H-imidazole-4-carboxylate: In a microwave vial was added ethyl 1H-imidazole-4-carboxylate (500 mg, 3.57 mmol, 1 equiv.), 2-fluorobenzonitrile (1.17 g, 906 µL, 7.14 mmol, 2 equiv.), K₂CO₃ (987 mg, 7.14 mmol, 2 equiv.) and DMSO (10 mL). Vial was sealed and mixture irradiated for 30 min. at 150° C., allowed to cool to RT, poured in 250 mL of water. Product was extracted 3×75 mL DCM, organic extracts were pooled, washed 3×250 mL water, 3×100 mL sat. aq. NaCl, dried (MgSO₄), filtered, filtrate evaporated. Amber oil was dried under high vacuum 1 hr. Product started to crystallize after a few minutes to give the title compound 962 mg (95%) amber crystalline solid. m/z (M+H)⁺=285.3; RT=1.41 min; purity=96.3%. HPLC conditions: Column: XBridge C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.29 (t, J=7.1 Hz, 3H), 4.27 (q, J=7.1 Hz, 2H), 7.69 (d, J=7.8 Hz, 1H), 7.83-7.72 (m, 1H), 7.89 (td, J=7.7, 0.9 Hz, 1H), 8.02-7.96 (m, 3H), 8.13 (d, J=0.6 Hz, 1H).

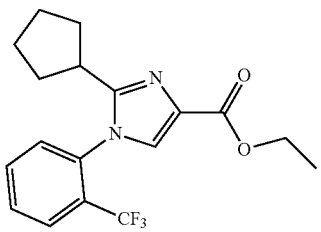 [SMILES: CCOC(=O)c1cn(-c2ccccc2C(F)(F)F)c(C2CCCC2)n1]

Ethyl 2-cyclopentyl-1-(2-(trifluoromethyl)phenyl)-1H-imidazole-4-carboxylate: Ethyl 1-(2-(trifluoromethyl)phenyl)-1H-imidazole-4-carboxylate (500 mg, 1.76 mmol, 1 equiv.) was added to a mixture of silver nitrate (179 mg, 1.06 mmol, 0.6 equiv.) and cyclopentane carboxylic acid (602 mg, 572 µL, 5.28 mmol, 3 equiv.) in 10% aqueous H₂SO₄ (6 mL), and the reaction mixture was heated at 90° C. A freshly prepared solution of ammonium persulfate (1.21 g, 5.28 mmol, 3 equiv.) in water (6 mL) was added drop-wise over ca. 20 minutes. The heating source was then removed and the reaction proceeded with evolution of carbon dioxide. After 1 hr, the reaction was terminated by pouring it onto ice/water (ca. 100 ml). The resulting mixture was made alkaline with 30% NH₄OH solution and extracted with ethyl acetate (2×50 mL). The combined extracts were washed with sat. aqueous NaCl (2×50 mL), dried (MgSO₄) and filtered. The filtrate was evaporated in vacuo, residue purified Combi-Flash, 40 g silica column, DCM isocratic 2 min. then to 15% methanol/DCM in 15 min. Purest fractions were pooled, solvent evaporated. Residue dried under high vacuum overnight to give the title compound, 125 mg (20%) as an amorphous amber solid. m/z (M+H)⁺=353.3; RT=1.71 min; purity=89.2%. HPLC conditions: Column: XBridge C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.27 (t, J=7.1 Hz, 3H), 1.48-1.38 (m, 2H), 1.77-1.58 (m, 5H), 1.86-1.78 (m, 1H), 2.59 (q, J=8.1 Hz, 1H), 4.30-4.17 (m, 2H), 7.67 (d, J=7.8 Hz, 1H), 7.81 (t, J=7.7 Hz, 1H), 7.89 (td, J=7.7, 1.0 Hz, 1H), 7.93 (d, J=0.7 Hz, 1H), 7.99 (dd, J=7.8, 1.1 Hz, 1H).

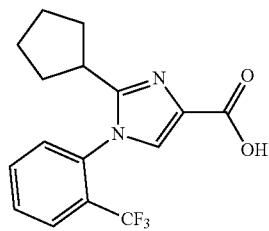 [SMILES: O=C(O)c1cn(-c2ccccc2C(F)(F)F)c(C2CCCC2)n1]

2-Cyclopentyl-1-(2-(trifluoromethyl)phenyl)-1H-imidazole-4-carboxylic acid: To a stirred THF (6 ml) sol. of ethyl 2-cyclopentyl-1-(2-(trifluoromethyl)phenyl)-1H-imidazole-4-carboxylate (123 mg, 0.35 mmol, 1 equiv.) was added LiOH—H₂O (17.6 mg, 0.42 mmol, 1.2 equiv.) followed by methanol (3 ml) and water (3 ml). LiOH was not completely soluble, more water (ca. 1.5 ml) was added and sol. was heated to 50° C. overnight. Allowed to cool to RT, organic solvents were evaporated, aq. sol. was diluted with 10 ml water, aq. 1N HCl (420 uL, 1.2 equiv.) was added, product extracted 2×10 ml ethyl acetate. Organic extracts were pooled, washed 10 ml sat. aq. NaCl, dried (MgSO₄), filtered, filtrate evaporated, residue dried under high vacuum. Yields title compound 115 mg (101%) as an amorphous solid. m/z (M+H)⁺=325.3; RT=1.37 min; purity=82.2%. HPLC conditions: Column: XBridge C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.50-1.35 (m, 2H), 1.80-1.55 (m, 6H), 2.62-2.54 (m, 1H), 7.86-7.72 (m, 2H), 7.89 (td, J=7.7, 1.0 Hz, 1H), 8.01-7.97 (m, 1H), 13.2-11.2 (s, broad, 1H),

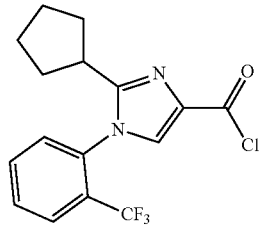 [SMILES: O=C(Cl)c1cn(-c2ccccc2C(F)(F)F)c(C2CCCC2)n1]

2-Cyclopentyl-1-(2-(trifluoromethyl)phenyl)-1H-imidazole-4-carbonyl chloride: 2-Cyclopentyl-1-(2-(trifluoromethyl)phenyl)-1H-imidazole-4-carboxylic acid (67 mg, 0.19 mmol) was dissolved in thionyl chloride (1.5 mL). Sol. was stirred and heated to 60° C. under nitrogen for 4 hrs. Allowed to cool to RT, volatiles were evaporated, residue was dissolved in 10 ml dioxane, sol. evaporated to dryness, residue dried under high vacuum 1 hr. Yields title compound 68 mg (105%) as an amber oil. Crude product was used as such for next transformation.

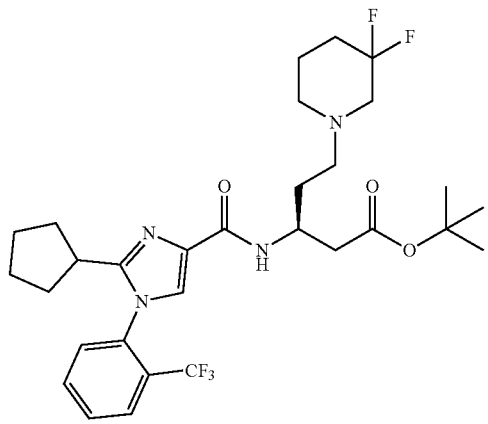 [SMILES: CC(C)(C)OC(=O)C[C@H](CCN1CCCC(F)(F)C1)NC(=O)c1cn(-c2ccccc2C(F)(F)F)c(C2CCCC2)n1]

(S)-tert-butyl 3-(2-cyclopentyl-1-(2-(trifluoromethyl) phenyl)-1H-imidazole-4-carboxamido)-5-(3,3-difluoropiperidin-1-yl)pentanoate: To a stirred, ice cold DCM (4 mL) sol. of (S)-tert-butyl 3-amino-5-(3,3-difluoropiperidin-1-yl) pentanoate (56 mg, 0.19 mmol, 1 equiv.) under nitrogen was added diisopropylethylamine (49 mg, 66 µL, 0.38 mmol, 2 equiv.) followed drop-wise by a DCM (1 ml) sol. of 2-cyclopentyl-1-(2-(trifluoromethyl)phenyl)-1H-imidazole-4-carbonyl chloride (65 mg, 0.19 mmol, 1 equiv.) Mixture was stirred 30 min. in the cold, allowed to warm to RT, stirred overnight. Dilute with 30 ml DCM, wash 2×10 ml sat. aq. NaHCO₃, 10 ml sat. aq. NaCl, sol. dried (MgSO₄), filtered, filtrate evaporated. Residue was purified Combi-Flash, 12 g column, DCM isocratic 2 min then to 10% MeOH/DCM in 10 min., purest fractions were pooled and solvent evaporated. Residue was dried under high vacuum to yield the title compound 37 mg (32%) as an amorphous solid. m/z (M+H)⁺ =599.5; RT=1.88 min; purity=97.6%. HPLC conditions: Column: XBridge C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.40-1.33 (rotamers, 2s, 9H), 1.50-1.41 (m, 2H), 1.93-1.55 (m, 11H), 2.72-2.28 (m, 10H), 4.35-4.23 (m, 1H), 7.67-7.59 (m, 2H), 7.76-7.68 (m, 1H), 7.80 (t, J=7.7 Hz, 1H), 7.89 (t, J=7.7 Hz, 1H), 7.98 (d, J=7.9 Hz, 1H).

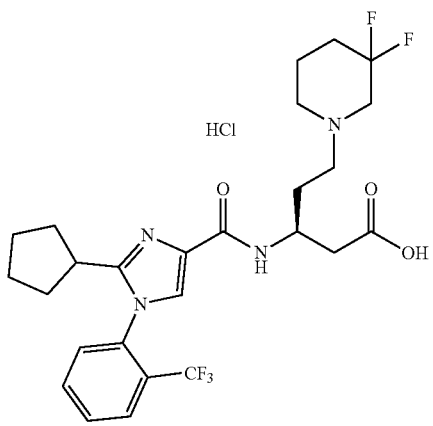 [SMILES: O=C(O)C[C@H](CCN1CCCC(F)(F)C1)NC(=O)c1cn(-c2ccccc2C(F)(F)F)c(C2CCCC2)n1 ; Cl]

(S)-3-(2-cyclopentyl-1-(2-(trifluoromethyl)phenyl)-1H-imidazole-4-carboxamido)-5-(3,3-difluoropiperidin-1-yl) pentanoic acid hydrochloride: To a stirred dioxane (500 µL) sol. of (S)-tert-butyl 3-(2-cyclopentyl-1-(2-(trifluoromethyl) phenyl)-1H-imidazole-4-carboxamido)-5-(3,3-difluoropiperidin-1-yl)pentanoate (33 mg, 0.055 mmol, 1 equiv.) under nitrogen was added 1 ml of a 4N HCl/dioxane sol. Resulting sol. stirred at RT 4 hrs. Solvent was evaporated to yield an amber oil, t-BuOMe (10 mL) was added, mixture sonicated 10 min., solvent evaporated to yield the title compound, 34 mg (107%) as a brownish solid. m/z (M+H)⁺=543.3; R_T=1.42 min; purity=97.1%. HPLC conditions: Column: XBridge C18, 3.5 µm, 4.630 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

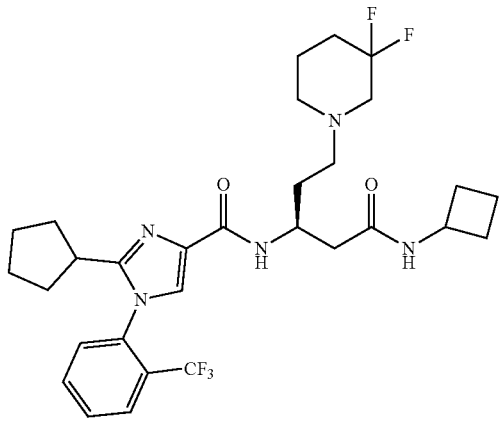 [SMILES: O=C(C[C@H](CCN1CCCC(F)(F)C1)NC(=O)c1cn(-c2ccccc2C(F)(F)F)c(C2CCCC2)n1)NC1CCC1]

(S)—N-(1-(cyclobutylamino)-5-(3,3-difluoropiperidin-1-yl)-1-oxopentan-3-yl)-2-cyclopentyl-1-(2-(trifluoromethyl) phenyl)-1H-imidazole-4-carboxamide: To a stirred DMF (500 µL) sol. of (S)-3-(2-cyclopentyl-1-(2-(trifluoromethyl) phenyl)-1H-imidazole-4-carboxamido)-5-(3,3-difluoropiperidin-1-yl)pentanoic acid hydrochloride (10 mg, 0.018 mmol, 1 equiv.) under nitrogen was added HATU (8.6 mg, 0.023 mmol, 1.25 equiv.), HOAt (3.1 mg, 0.023 mmol, 1.25 equiv.), DIPEA (9.3 mg, 0.072 mmol, 12.5 µL, 4 equiv.) and cyclobutylamine (1.95 mg, 0.027 mmol, 2.34 µL, 1.5 equiv.). Sol. was stirred overnight (16 hrs), it was next diluted with ethyl acetate (c.a. 30 ml), washed 3×20 ml sat. aq. NaHCO₃, 20 ml sat. aq. NaCl, dried (MgSO₄), filtered, filtrate evaporated. Residue was purified Combi-Flash, reverse phase 12 g C18 column, 10 mM ammonium carbonate isocratic 2 min. then to 100% acetonitrile in 15 min. Purest fractions were pooled, acetonitrile evaporated, remaining aqueous suspension was transferred in a tared vial, flask rinsed 2×1 ml acetonitrile, washings combined with aqueous suspension (clear solution obtained). Sol. was frozen and lyophilized to yield the title compound, 6.2 mg (58%) as a white solid. m/z (M+H)⁺=596.2; R_T=1.56 min; purity=99.0%. HPLC conditions: Column: XBridge C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.50-1.40 (m, 2H), 1.78-1.55 (m, 10H), 1.92-1.79 (m, 4H), 2.18-2.05 (m, 2H), 2.45-2.25 (m, 6H), 2.75-2.48 (m, 5H), 4.30-4.12 (m, 2H), 7.67-7.60 (m, 2H), 7.80 (t, J=7.7 Hz, 1H), 7.88 (t, J=7.7 Hz, 1H), 8.00-7.93 (m, 2H), 8.20-8.14 (m, 1H).

Characterization of the Apelin Agonist Activity of the Compounds

The compounds above were studied for their in vitro activity as apelin agonists using the methods described by Giddings et al. Giddings et al., 2010 Int J High Thro Screen. 1:39-47, the contents of which are hereby incorporated by reference in its entirety. The methods described in Giddings et al. were used as described and Apelin-13 was a positive control.

TABLE 1
| ID # | STRUCTURE | [M + H]+/[M − H]− |
|---|---|---|
| 444 | 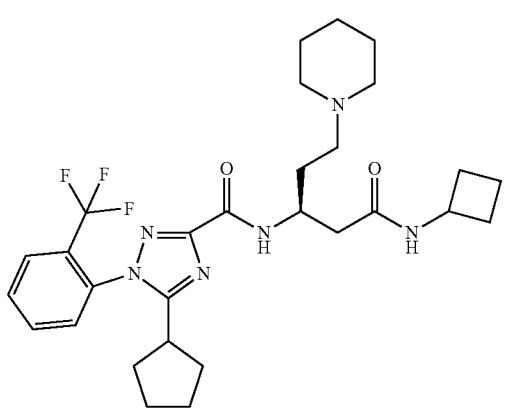 [SMILES: O=C(C[C@H](CCN1CCCCC1)NC(=O)c1nc(C2CCCC2)n(-c2ccccc2C(F)(F)F)n1)NC1CCC1] | 561.5 |
| 446 | 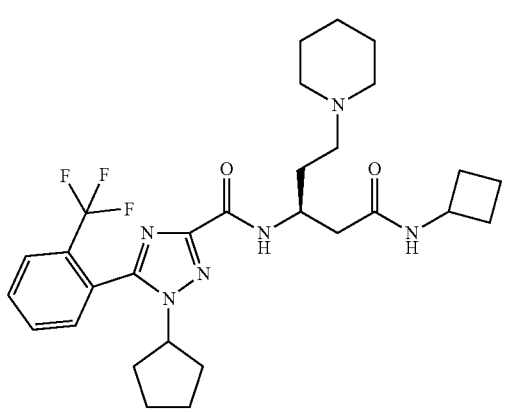 [SMILES: O=C(C[C@H](CCN1CCCCC1)NC(=O)c1nc(-c2ccccc2C(F)(F)F)n(C2CCCC2)n1)NC1CCC1] | 561.5 |
| 453 | 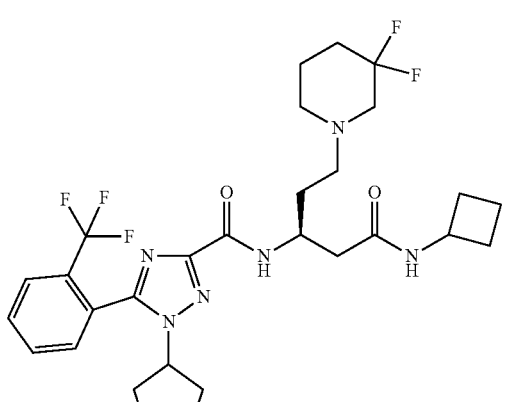 | 595.3 |

TABLE 1-continued
| ID # | STRUCTURE | [M + H]+/[M − H]− |
|---|---|---|
| 454 | 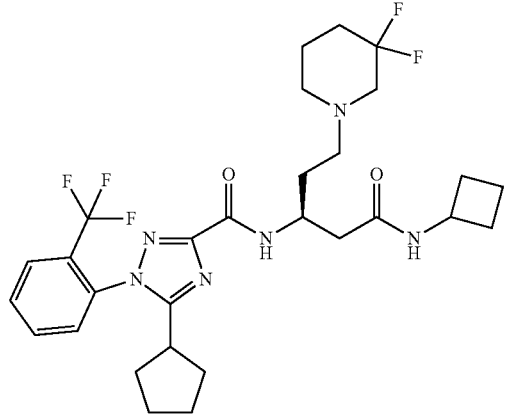 [SMILES: O=C(C[C@H](CCN1CCCC(F)(F)C1)NC(=O)c1nc(C2CCCC2)n(-c2ccccc2C(F)(F)F)n1)NC1CCC1] | 597.3 |
| 455 | 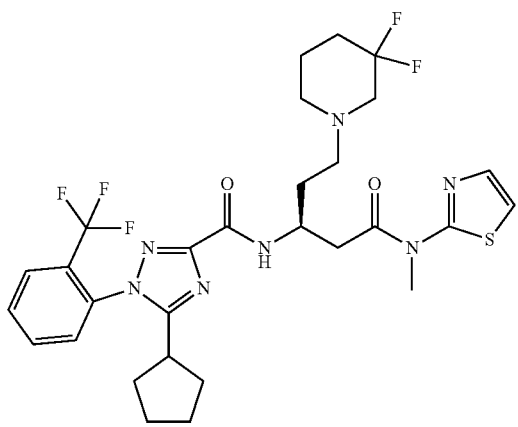 [SMILES: CN(C(=O)C[C@H](CCN1CCCC(F)(F)C1)NC(=O)c1nc(C2CCCC2)n(-c2ccccc2C(F)(F)F)n1)c1nccs1] | 640.3 |
| 456 | 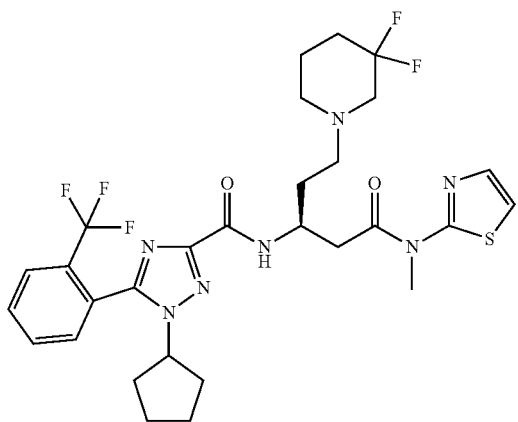 [SMILES: CN(C(=O)C[C@H](CCN1CCCC(F)(F)C1)NC(=O)c1nc(-c2ccccc2C(F)(F)F)n(C2CCCC2)n1)c1nccs1] | 640.3 |

TABLE 1-continued
| ID # | STRUCTURE | [M + H]+/[M − H]− |
|---|---|---|
| 461 | 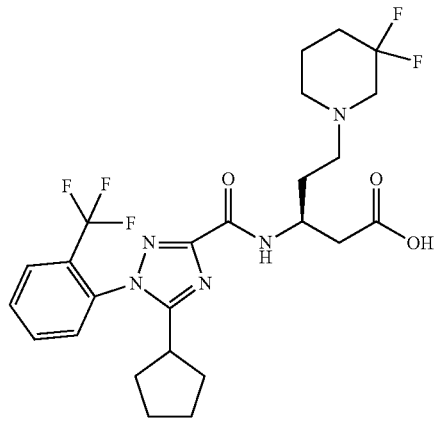 [SMILES: O=C(O)C[C@H](CCN1CCCC(F)(F)C1)NC(=O)c1nc(C2CCCC2)n(-c2ccccc2C(F)(F)F)n1] | 544.2 |
| 462 | 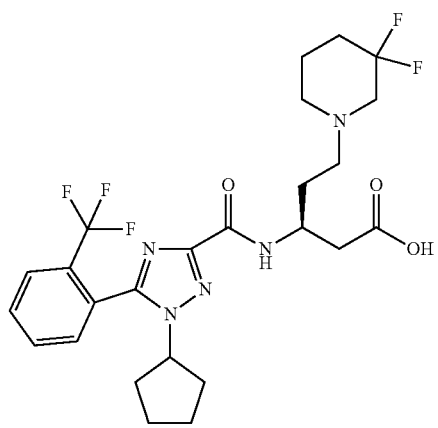 [SMILES: O=C(O)C[C@H](CCN1CCCC(F)(F)C1)NC(=O)c1nc(-c2ccccc2C(F)(F)F)n(C2CCCC2)n1] | 544.2 |
| 472 | 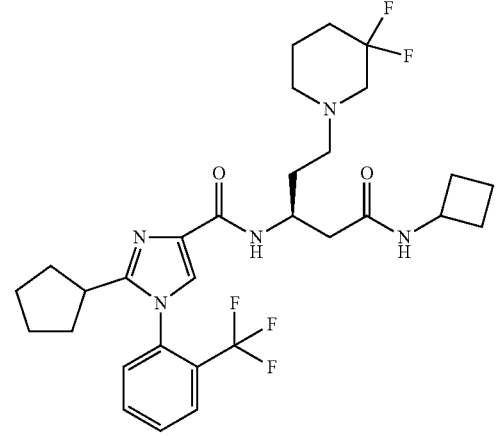 [SMILES: O=C(C[C@H](CCN1CCCC(F)(F)C1)NC(=O)c1cn(-c2ccccc2C(F)(F)F)c(C2CCCC2)n1)NC1CCC1] | 596.2 |

TABLE 1-continued
| ID # | STRUCTURE | [M + H]+/[M − H]− |
|---|---|---|
| 473 | 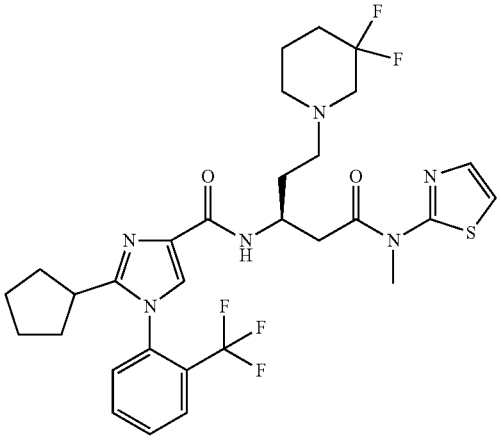 [SMILES: CN(C(=O)C[C@H](CCN1CCCC(F)(F)C1)NC(=O)c1cn(-c2ccccc2C(F)(F)F)c(C2CCCC2)n1)c1nccs1] | 639.3 |
| 474 | 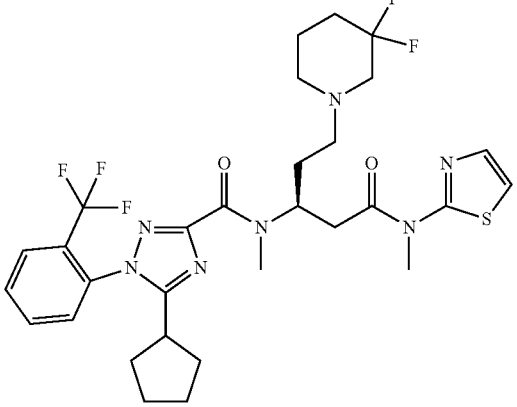 | 654.2 |
| 476 | 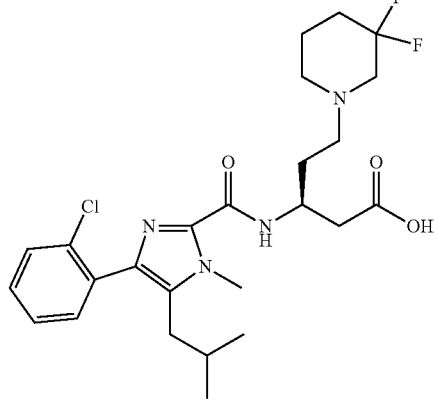 | 511.2 |

TABLE 1-continued
| ID # | STRUCTURE | [M + H]+/[M − H]− |
|---|---|---|
| 477 | 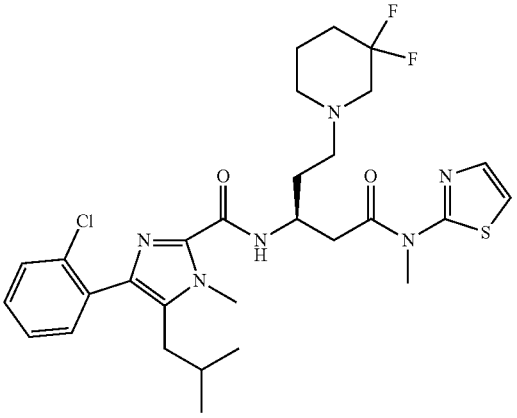 [SMILES: CC(C)Cc1c(-c2ccccc2Cl)nc(C(=O)N[C@@H](CCN2CCCC(F)(F)C2)CC(=O)N(C)c2nccs2)n1C] | 607.3 |
| 478 | 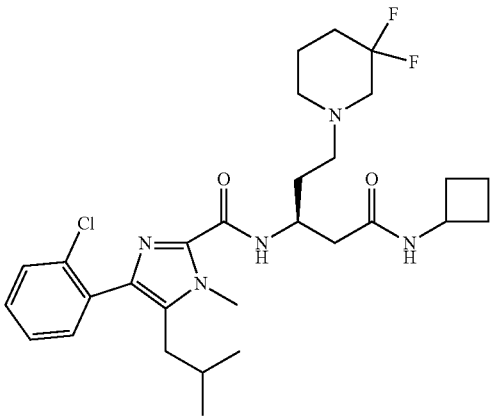 [SMILES: CC(C)Cc1c(-c2ccccc2Cl)nc(C(=O)N[C@@H](CCN2CCCC(F)(F)C2)CC(=O)NC2CCC2)n1C] | 564.4 |
| 512 | 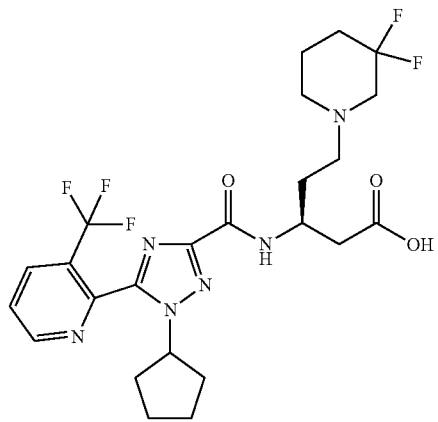 [SMILES: O=C(O)C[C@H](CCN1CCCC(F)(F)C1)NC(=O)c1nc(-c2ncccc2C(F)(F)F)n(C2CCCC2)n1] | 545.3 |

TABLE 1-continued
| ID # | STRUCTURE | [M + H]+/[M − H]− |
|---|---|---|
| 513 | 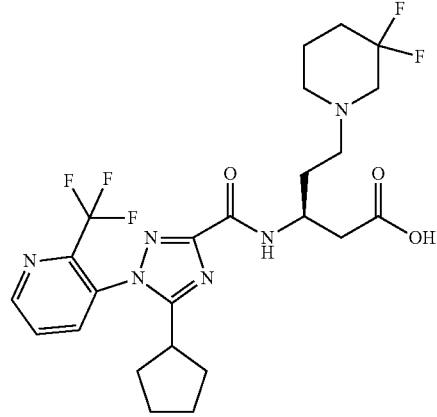 [SMILES: O=C(O)C[C@H](CCN1CCCC(F)(F)C1)NC(=O)c1nc(C2CCCC2)n(-c2cccnc2C(F)(F)F)n1] | 545.2 |
| 530 | 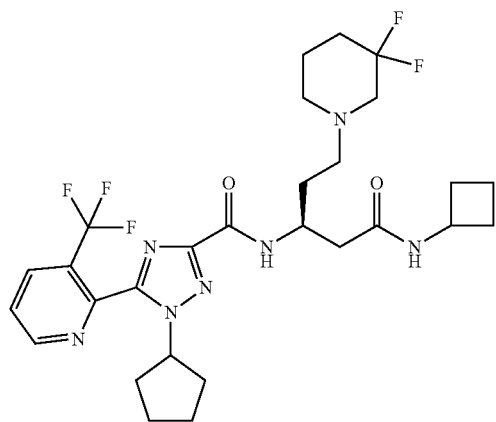 [SMILES: O=C(C[C@H](CCN1CCCC(F)(F)C1)NC(=O)c1nc(-c2ncccc2C(F)(F)F)n(C2CCCC2)n1)NC1CCC1] | 598.3 |
| 531 | 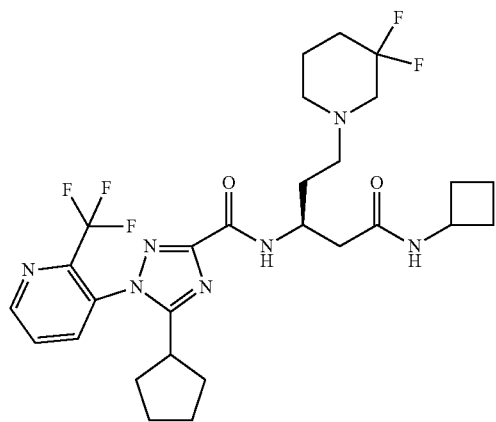 [SMILES: O=C(C[C@H](CCN1CCCC(F)(F)C1)NC(=O)c1nc(C2CCCC2)n(-c2cccnc2C(F)(F)F)n1)NC1CCC1] | 598.3 |

TABLE 1-continued
| ID # | STRUCTURE | [M + H]+/[M − H]− |
|------|-----------|-------------------|
| 532 | 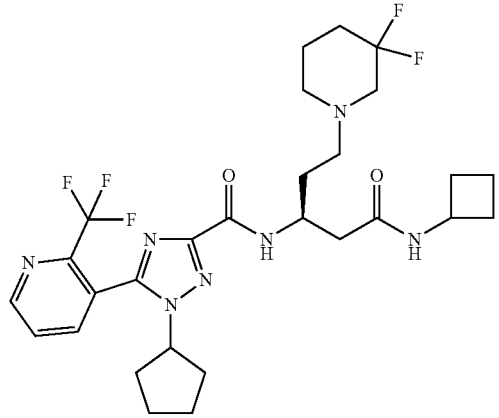 [SMILES: O=C(C[C@H](CCN1CCCC(F)(F)C1)NC(=O)c1nc(-c2cccnc2C(F)(F)F)n(C2CCCC2)n1)NC1CCC1] | 598.4 |
| 543 | 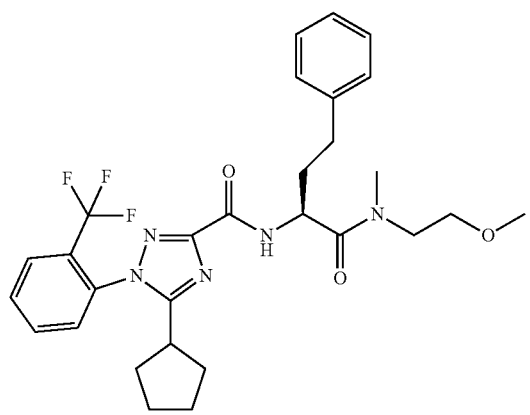 [SMILES: COCCN(C)C(=O)[C@H](CCc1ccccc1)NC(=O)c1nc(C2CCCC2)n(-c2ccccc2C(F)(F)F)n1] | 558.2 |
| 564 | 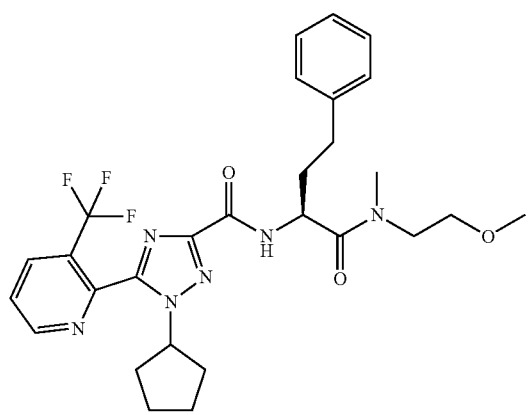 [SMILES: COCCN(C)C(=O)[C@H](CCc1ccccc1)NC(=O)c1nc(-c2ncccc2C(F)(F)F)n(C2CCCC2)n1] | 559.3 |

TABLE 1-continued
| ID # | STRUCTURE | [M + H]+/[M − H]− |
|---|---|---|
| 569 | 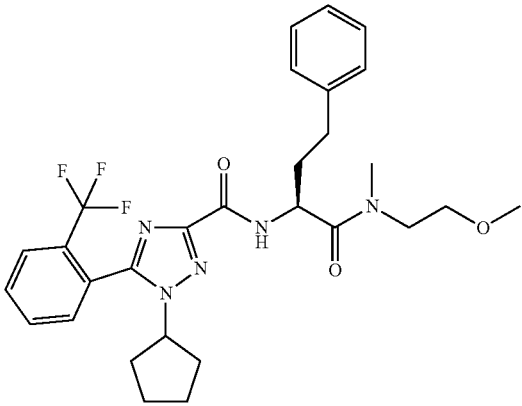 [SMILES: COCCN(C)C(=O)[C@H](CCc1ccccc1)NC(=O)c1nc(-c2ccccc2C(F)(F)F)n(C2CCCC2)n1] | 558.3 |
| 586 | 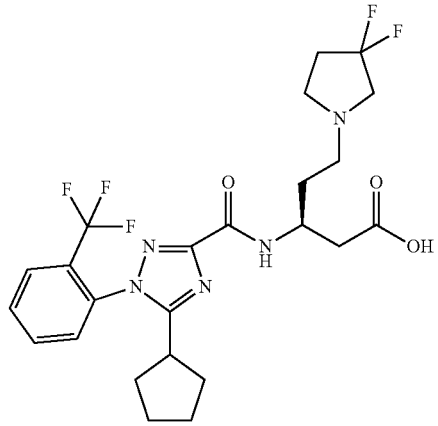 [SMILES: O=C(O)C[C@H](CCN1CCC(F)(F)C1)NC(=O)c1nc(C2CCCC2)n(-c2ccccc2C(F)(F)F)n1] | 530.3 |
| 616 | 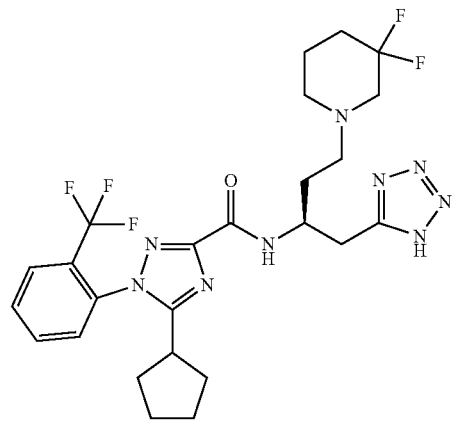 [SMILES: O=C(N[C@@H](CCN1CCCC(F)(F)C1)Cc1nnn[nH]1)c1nc(C2CCCC2)n(-c2ccccc2C(F)(F)F)n1] | 567.6 |

TABLE 1-continued
| ID # | STRUCTURE | [M + H]+/ [M − H]− |
|---|---|---|
| 617 | 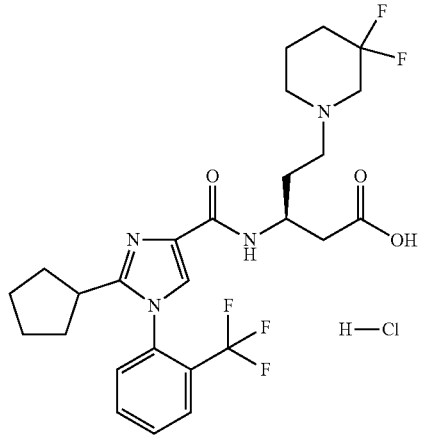 [SMILES: O=C(O)C[C@H](CCN1CCCC(F)(F)C1)NC(=O)c1cn(-c2ccccc2C(F)(F)F)c(C2CCCC2)n1 ; Cl] H—Cl | 543.3 |
| 620 | 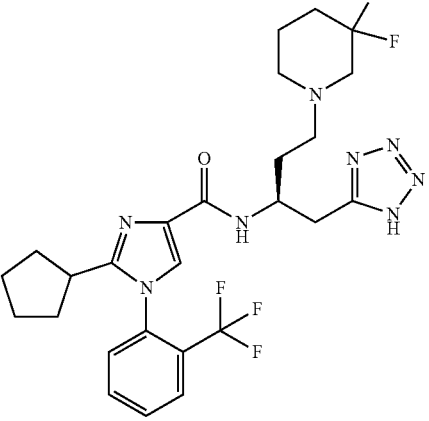 | 567.4 |
| 662 | 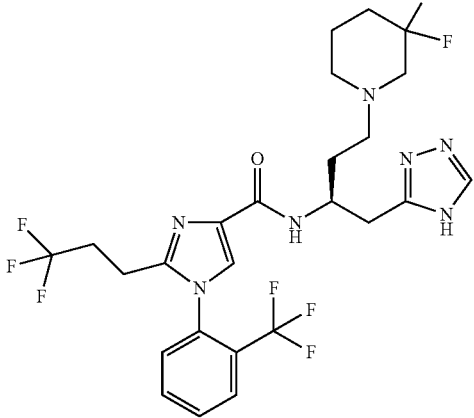 | 594.2 |

TABLE 1-continued
| ID # | STRUCTURE | [M + H]+/[M − H]− |
|---|---|---|
| 669 | 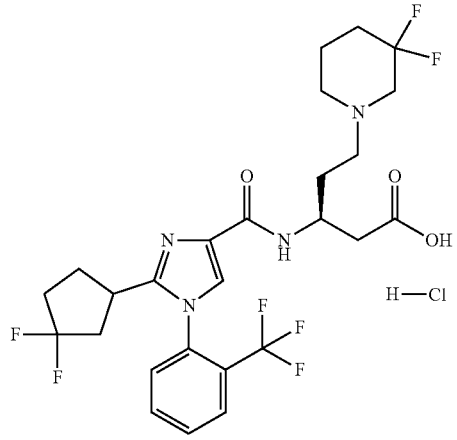 | 579.4 |
| 670 | 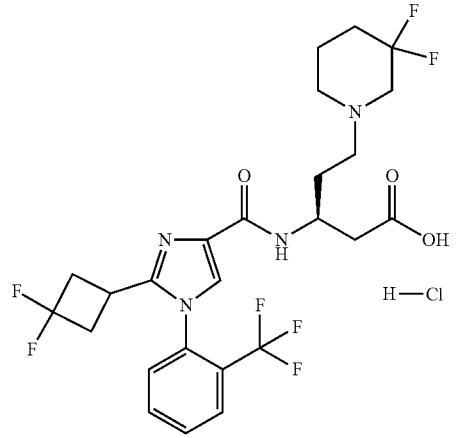 | 565.4 |
| 672 | 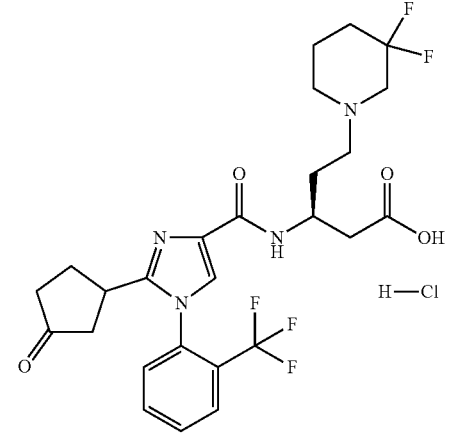 | 557.4 |

TABLE 1-continued
| ID # | STRUCTURE | [M + H]+/[M − H]− |
|---|---|---|
| 673 | 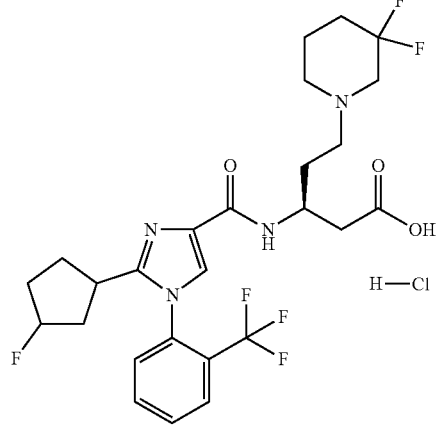 | 561.3 |
| 674 | 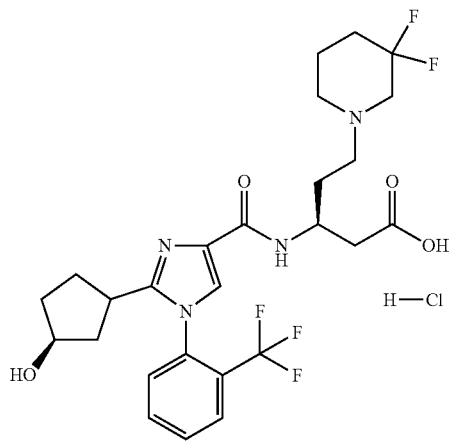 | 559.3 |
| 677 | 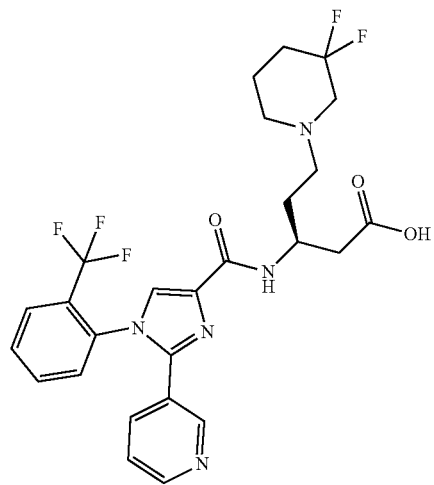 [SMILES: O=C(O)C[C@H](CCN1CCCC(F)(F)C1)NC(=O)c1cn(-c2ccccc2C(F)(F)F)c(-c2cccnc2)n1] | 552.4 |

TABLE 1-continued

| ID # | STRUCTURE | [M + H]+/[M − H]− |
|---|---|---|
| 678 | 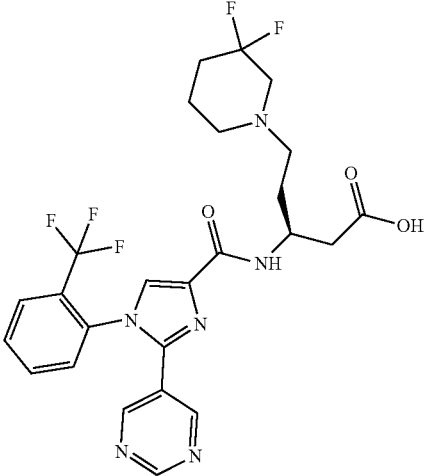 [SMILES: O=C(O)C[C@H](CCN1CCCC(F)(F)C1)NC(=O)c1cn(-c2ccccc2C(F)(F)F)c(-c2cncnc2)n1] | 553.3 |
| 679 | 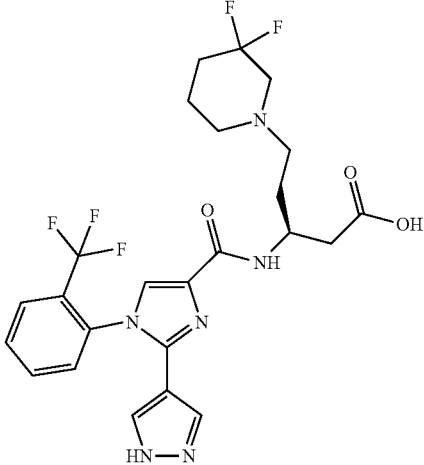 [SMILES: O=C(O)C[C@H](CCN1CCCC(F)(F)C1)NC(=O)c1cn(-c2ccccc2C(F)(F)F)c(-c2cn[nH]c2)n1] | 541.3 |

TABLE 2

| ID# | IUPAC Name | EC50 (nM) Ave |
|---|---|---|
| 444 | (3S)-N-cyclobutyl-3-({5-cyclopentyl-1-[2-(trifluoromethyl)phenyl]-1H-1,2,4-triazol-3-yl}formamido)-5-(piperidin-1-yl)pentanamide | 40 |
| 446 | (3S)-N-cyclobutyl-3-({1-cyclopentyl-5-[2-(trifluoromethyl)phenyl]-1H-1,2,4-triazol-3-yl}formamido)-5-(piperidin-1-yl)pentanamide | 310 |
| 453 | (3S)-N-cyclobutyl-3-({1-cyclopentyl-5-[2-(trifluoromethyl)phenyl]-1H-1,2,4-triazol-3-yl}formamido)-5-(3,3-difluoropiperidin-1-yl)pentanamide | 9 |
| 454 | (3S)-N-cyclobutyl-3-({5-cyclopentyl-1-[2-(trifluoromethyl)phenyl]-1H-1,2,4-triazol-3-yl}formamido)-5-(3,3-difluoropiperidin-1-yl)pentanamide | 8.3 |
| 455 | (3S)-3-({5-cyclopentyl-1-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide | 22 |
| 456 | (3S)-3-({1-cyclopentyl-5-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide | 48 |
| 461 | (3S)-3-({5-cyclopentyl-1-[2-(trifluoromethyl)phenyl]-1H-1,2,4-triazol-3-yl}formamido)-5-(3,3-difluoropiperidin-1-yl)pentanoic acid | 46 |
| 462 | (3S)-3-({1-cyclopentyl-5-[2-(trifluoromethyl)phenyl]-1H-1,2,4-triazol-3-yl}formamido)-5-(3,3-difluoropiperidin-1-yl)pentanoic acid | 384 |
| 472 | (3S)-N-cyclobutyl-3-({2-cyclopentyl-1-[2-(trifluoromethyl)phenyl]-1H-imidazol-4-yl}formamido)-5-(3,3-difluoropiperidin-1-yl)pentanamide | 15 |
| 473 | (3S)-3-({2-cyclopentyl-1-[2-(trifluoromethyl)phenyl]-1H-imidazol-4-yl}formamido)-5-(3,3-difluoropiperidin-1-yl)-N-methyl-N-(1,3-thiazol-2-yl)pentanamide | 46 |

TABLE 2-continued

| ID# | IUPAC Name | EC50 (nM) Ave |
|---|---|---|
| 474 | (3S)-3-(1-{5-cyclopentyl-1-[2-(trifluoromethyl)phenyl]-1H-1,2,4-triazol-3-yl}-N-methylformamido)-5-(3,3-difluoropiperidin-1-yl)-N-methyl-N-(1,3-thiazol-2-yl)pentanamide | 588 |
| 476 | (3S)-3-{[4-(2-chlorophenyl)-1-methyl-5-(2-methylpropyl)-1H-imidazol-2-yl]formamido}-5-(3,3-difluoropiperidin-1-yl)pentanoic acid | >10,000 |
| 477 | (3S)-3-{[4-(2-chlorophenyl)-1-methyl-5-(2-methylpropyl)-1H-imidazol-2-yl]formamido}-5-(3,3-difluoropiperidin-1-yl)-N-methyl-N-(1,3-thiazol-2-yl)pentanamide | >10,000 |
| 478 | (3S)-3-{[4-(2-chlorophenyl)-1-methyl-5-(2-methylpropyl)-1H-imidazol-2-yl]formamido}-N-cyclobutyl-5-(3,3-difluoropiperidin-1-yl)pentanamide | >10,000 |
| 512 | (3S)-3-({1-cyclopentyl-5-[3-(trifluoromethyl)pyridin-2-yl]-1H-1,2,4-triazol-3-yl}formamido)-5-(3,3-difluoropiperidin-1-yl)pentanoic acid | 152 |
| 513 | (3S)-3-({5-cyclopentyl-1-[2-(trifluoromethyl)pyridin-3-yl]-1H-1,2,4-triazol-3-yl}formamido)-5-(3,3-difluoropiperidin-1-yl)pentanoic acid | >10,000 |
| 530 | (3S)-N-cyclobutyl-3-({1-cyclopentyl-5-[3-(trifluoromethyl)pyridin-2-yl]-1H-1,2,4-triazol-3-yl}formamido)-5-(3,3-difluoropiperidin-1-yl)pentanamide | 7.5 |
| 531 | (3S)-N-cyclobutyl-3-({5-cyclopentyl-1-[2-(trifluoromethyl)pyridin-3-yl]-1H-1,2,4-triazol-3-yl}formamido)-5-(3,3-difluoropiperidin-1-yl)pentanamide | 323 |
| 532 | (3S)-N-cyclobutyl-3-({1-cyclopentyl-5-[2-(trifluoromethyl)pyridin-3-yl]-1H-1,2,4-triazol-3-yl}formamido)-5-(3,3-difluoropiperidin-1-yl)pentanamide | 2537 |
| 543 | (2S)-2-({5-cyclopentyl-1-[2-(trifluoromethyl)phenyl]-1H-1,2,4-triazol-3-yl}formamido)-N-(2-methoxyethyl)-N-methyl-4-phenylbutanamide | 754 |
| 569 | (2S)-2-({1-cyclopentyl-5-[2-(trifluoromethyl)phenyl]-1H-1,2,4-triazol-3-yl}formamido)-N-(2-methoxyethyl)-N-methyl-4-phenylbutanamide | >10,000 |
| 586 | (3S)-3-({5-cyclopentyl-1-[2-(trifluoromethyl)phenyl]-1H-1,2,4-triazol-3-yl}formamido)-5-(3,3-difluoropyrrolidin-1-yl)pentanoic acid | 74 |
| 616 | 5-cyclopentyl-N-[(2S)-4-(3,3-difluoropiperidin-1-yl)-1-(1H-1,2,3,4-tetrazol-5-yl)butan-2-yl]-1-[2-(trifluoromethyl)phenyl]-1H-1,2,4-triazole-3-carboxamide | 9 |
| 617 | (3S)-3-({2-cyclopentyl-1-[2-(trifluoromethyl)phenyl]-1H-imidazol-4-yl}formamido)-5-(3,3-difluoropiperidin-1-yl)pentanoic acid | 13 |
| 620 | 2-cyclopentyl-N-[(2S)-4-(3,3-difluoropiperidin-1-yl)-1-(1H-1,2,3,4-tetrazol-5-yl)butan-2-yl]-1-[2-(trifluoromethyl)phenyl]-1H-imidazole-4-carboxamide | 8 |

5.2. Cellular Uptake Assay

Caco-2 cells (clone $C_2BBe1$) were obtained from American Type Culture Collection (Manassas, VA). Cell monolayers were grown to confluence on collagen-coated, microporous, polycarbonate membranes in 12-well Costar Transwell plates. Details of the plates and their certification are shown below. The permeability assay buffer was Hanks' balanced salt solution (HBSS) containing 10 mM HEPES and 15 mM glucose at a pH of 7.4. The buffer in the receiver chamber also contained 1% bovine serum albumin. The dosing solution concentration was 5 μM for each test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. After the experiment, all assay buffers were removed from the inserts. Cell monolayers were dosed with blank 500 μM lucifer yellow on the A-to-B side and blank HBSS on the B-to-A side and incubated at 37° C. Samples were taken from the B-to-A side at 60 minutes. The flux of lucifer yellow was measured for each monolayer to ensure no damage was inflicted to the cell monolayers during the flux period. All samples were analyzed by LC-MS/MS using electrospray ionization. The apparent permeability ($P_{app}$) and percent recovery were calculated as follows:

$$P_{app} = (dC_r/d_t) \times V_r/(A \times C_A) \quad (1)$$

$$\text{Percent Recovery} = 100 \times ((V_r \times C_r^{final}) + (V_d \times C_d^{final}))/(V_d \times C_N) \quad (2)$$

Where, $dC_r/dt$ is the slope of the cumulative concentration in the receiver compartment versus time in M s$^{-1}$;

$V_r$ is the volume of the receiver compartment in cm$^3$;

$V_d$ is the volume of the donor compartment in cm$^3$;

A is the area of the insert (1.13 cm$^2$ for 12-well Transwell);

$C_A$ is the average of the nominal dosing concentration and the measured 120-minute donor concentration in μM;

$C_N$ is the nominal concentration of the dosing solution in M;

$C_r^{final}$ is the cumulative receiver concentration in M at the end of the incubation period;

$C_d^{final}$ is the concentration of the donor in μM at the end of the incubation period.

Efflux ratio (ER) is defined as $P_{app}$ (B-to-A)/$P_{app}$ (A-to-B).

Absorption Potential Classification:
$P_{app}$ (A-to-B) < $1.0 \times 10^{-6}$ cm/s: Low
$P_{app}$ (A-to-B) ≥ $1.0 \times 10^{-6}$ cm/s: High
Significant Efflux is defined as: ER ≥ 2.0 and $P_{app}$ (B-to-A) ≥ $1.0 \times 10^{-6}$ cm/

| CP # | EC50 (nM) | Efflux ratio |
|---|---|---|
| 461 | 46 | 7 |
| 472 | 15 | 4 |
| 530 | 7.5 | 46 |
| 616 | 9 | 17 |

In Vivo Blood Pressure Lowering Activity of the Compounds

Related compounds were also assayed for blood pressure activity using C57B1L6 mice and the procedure described by Tatemoto et al. The novel peptide apelin lowers blood pressure via a nitric oxide-dependent mechanism. Regul Pept. 2001; 99: 87-92. The compounds were synthesized and characterized using the in vitro assays described above.

Studies have been published citing reductions in blood pressure occur following peptide apelin administration. Apelin-13 was used as a positive control. See WO 2015/188073 (Research Triangle Inst.) the contents of which are hereby incorporated by reference.

It is to be understood that, while the disclosure has been described in conjunction with the detailed description, thereof, the foregoing description is intended to illustrate and not limit the scope of the disclosure. Other aspects, advantages, and modifications of the disclosure are within the scope of the claims set forth below. All publications, patents, and patent applications cited in this specification are herein incorporated by reference as if each individual publication or patent application was specifically and individually indicated to be incorporated by reference.

What is claimed is:

1. A compound represented by the Formula I:

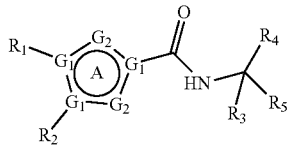

or a pharmaceutically acceptable salt, a prodrug, or a salt of a prodrug thereof, wherein ring A is a 5-member heteroaryl ring; each $G_1$ is independently selected from C or N;

each $G_2$ is independently selected from CH or N; the bond between each two instances of $G_1$ or $G_2$ is either a single or a double bond so as to make the ring A an aromatic heterocycle, wherein at least one $G_1$ or $G_2$ is N and a maximum number of three instances of either $G_1$ or $G_2$ in the ring are simultaneously N; provided that if there are two N in ring A and $G_1$ connected to $R_2$ or $R_1$ is N, the adjacent $G_2$ is not N;

$R_1$ is represented by the formula:

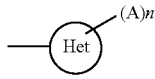

wherein

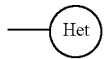

is a monocyclic aryl or heteroaryl group;

each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, $-CF_3$, $-(CH_2)_xNR_7R_8$, $-CN$, $-CONR_7R_8$, $-COR_7$, $-CO_2(CH_2)_xNR_7R_8$, $-CO_2R_7$, halogen, hydroxyl, $-N_3$, $-NHCOR_7$, $-NHSO_2C_{1-8}$ alkyl, $-NHCO_2C_{1-8}$ alkyl, $-NO_2$, $-NR_7R_8$, $-O(CH_2)_xNR_7R_8$, $-O(CH_2)_xCO_2R_7$, $-OCOC_{1-8}$ alkyl, $-OCO(CH_2)_xNR_7R_8$, $-SO_2NR_7R_8$, $-SO_{(1-3)}R_7$, or $-SR_7$;

$R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, $-(CH_2)_xCONHR_9$, $-(CH_2)_xCOR_9$, $-(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups;

n is 1, 2, 3, 4 or 5;

$R_2$ is optionally substituted $C_{3-8}$ alkyl or optionally substituted $C_{0-8}$ alkyl-$R_{10}$, wherein $R_{10}$ is a 3- to 8-membered ring, optionally containing one or more heteroatom selected from N, O, or S, optionally containing one or more degrees of unsaturation;

$R_3$ is H;

$R_4$ is adamantanyl, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl (aryl), $C_{2-8}$ alkenyl(heteroaryl), $C_{3-8}$ alkynyl, $C_{3-8}$ cycloalkyl-$CO_2R_7$, $-(CH_2)_xNR_7R_8$, $-(CH_2)_xOR_7$, $-(CH_2)_xNR_9COR_7$, $-(CH_2)_xNR_9SO_2R_7$, $-(CH_2)_xNR_9CO_2R_7$, $-(CH_2)_xNHCOR_7$, $-(CH_2)_xNHSO_2R_7$, $-(CH_2)_xNHCO_2R_7$, $-(CH_2)_{xx}CONR_7R_8$, $-(CH_2)_xCONR_7(CH_2)_yCO_2R_9$, $-(CH_2)_xCONR_7(CH_2)_yCONR_7R_8$, $-(CH_2)_xCONR_7(CH_2)_yR_9$, $-(CH_2)_xCOR_7$, $-(CH_2)_{xx}CO_2R_7$, $-(CH_2)_xSO_2NR_7(CH_2)_yR_9$, $-CHR_7COR_9$, $-CHR_7CONHCHR_8COR_9$, $-CONR_7(CH_2)_xCO_2R_8$, $-CONR_7CHR_8CO_2R_9$, $-NHCO_2R_7$, or $-(CH_2)_x SO_2NR_7R_8$;

$R_5$ is adamantanyl, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl (aryl), $C_{2-8}$ alkenyl(heteroaryl), $C_{3-8}$ alkynyl, $C_{5-8}$ cycloalkyl, $C_{3-8}$ cycloalkyl-$CO_2R_7$, $-(CH_2)_xNR_7R_8$, where at least one of $R_7$ or $R_8$ is not H, $-(CH_2)_xOR_7$, $-(CH_2)_xNR_9COR_7$, $-(CH_2)_xNR_9SO_2R_7$, $-(CH_2)_xNR_9CO_2R_7$, $-(CH_2)_xNHCOR_7$, $-(CH_2)_xNHSO_2R_7$, $-(CH_2)_xNHCO_2R_7$, $-(CH_2)_{xx}CONR_7R_8$, $-(CH_2)_xCONR_7(CH_2)_yCO_2R_9$, $-(CH_2)_xCONR_7(CH_2)_yCONR_7R_8$, $-(CH_2)_xCONR_7(CH_2)_yR_9$, $-(CH_2)_xCOR_7$, $-(CH_2)_{xx}CO_2R_7$, $-(CH_2)_xSO_2NR_7(CH_2)_yR_9$, $-CHR_7COR_9$, $-CHR_7CONHCHR_8COR_9$, $-CONR_7(CH_2)_xCO_2R_8$, $-CONR_7CHR_8CO_2R_9$, $-NHCO_2R_7$, or $-(CH_2)_x SO_2NR_7R_8$;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each x is independently 0-8;

each xx is independently 1-8; and each y is independently 1-8.

2. The compound of claim 1, wherein the compound of Formula I is
a) a compound of Formula IV:

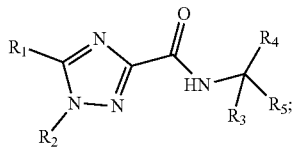
IV b) a compound of Formula V:

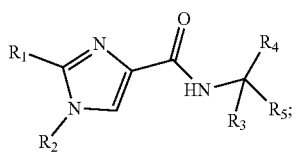
V or
c) a compound of Formula VI:

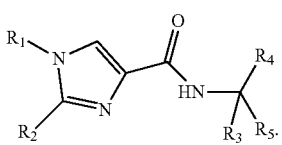
VI

3. The compound of claim 1, wherein

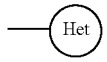

is a monocyclic aryl group;
wherein n is 1 or 2; each A is independently $C_{1-4}$ alkoxy, $C_{1-4}$ alkoxy aryl, or halogen;
$R_2$ is substituted aryl, unsubstituted heteroaryl, substituted heteroaryl, $C_{3-8}$ alkyl, or $C_{3-8}$ cycloalkyl;
$R_4$ is $C_{2-8}$ alkyl(aryl) or $C_{1-8}$ alkyl ($C_{3-8}$ cycloalkyl);
$R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_{xx}CO_2R_7$, —$CHR_7COR_9$, —$CHR_7CONHCHR_8COR_9$, or —$CONR_7(CH_2)_xCO_2R_8$;
$R_3$ is H;
$R_9$ is $C_{1-8}$ alkyl, H, or heteroaryl, which is an oxazole;
x is 1-4;
xx is 1-4; and
y is 1-3.

4. The compound of claim 1, wherein n is 1 or 2; each A is independently $C_1$ alkoxy, $C_1$ alkoxy aryl, or halogen;
$R_2$ is substituted aryl, unsubstituted heteroaryl, substituted heteroaryl, $C_4$ alkyl or $C_6$ cycloalkyl;
$R_4$ is $C_{2-8}$ alkyl(aryl), or $C_{1-8}$ alkyl ($C_{3-8}$ cycloalkyl);
$R_5$ is —$(CH_2)_xCNHCOR_7$, —$(CH_2)_xCNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_{xx}CO_2R_7$, —$CHR_7COR_9$, —$CHR_7CONHCHR_8COR_9$, or —$CONR_7(CH_2)_xCO_2R_8$;
$R_3$ is H;
$R_8$ is $C_{1-4}$ alkyl or H;
$R_9$ is $C_{1-8}$ alkyl, H, or heteroaryl which is an oxazole;
x is 1-4;
xx is 1-4; and
y is 1-3.

5. A compound selected from:
(3S)—N-cyclobutyl-3-({5-cyclopentyl-1-[2-(trifluoromethyl)phenyl]-1H-1,2,4-triazol-3-yl}formamido)-5-(piperidin-1-yl)pentanamide;
(3S)—N-cyclobutyl-3-({1-cyclopentyl-5-[2-(trifluoromethyl)phenyl]-1H-1,2,4-triazol-3-yl}formamido)-5-(piperidin-1-yl)pentanamide;
(3S)—N-cyclobutyl-3-({1-cyclopentyl-5-[2-(trifluoromethyl)phenyl]-1H-1,2,4-triazol-3-yl}formamido)-5-(3,3-difluoropiperidin-1-yl)pentanamide;
(3S)—N-cyclobutyl-3-({5-cyclopentyl-1-[2-(trifluoromethyl)phenyl]-1H-1,2,4-triazol-3-yl}formamido)-5-(3,3-difluoropiperidin-1-yl)pentanamide;
(3S)-3-({5-cyclopentyl-1-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide;
(3S)-3-({1-cyclopentyl-5-[2-(trifluoromethyl)phenyl]-1H-1,2,4-triazol-3-yl}formamido)-5-(3,3-difluoropiperidin-1-yl)-N-methyl-N-(1,3-thiazol-2-yl)pentanamide;
(3S)-3-({5-cyclopentyl-1-[2-(trifluoromethyl)phenyl]-1H-1,2,4-triazol-3-yl}formamido)-5-(3,3-difluoropiperidin-1-yl)pentanoic acid;
(3S)-3-({1-cyclopentyl-5-[2-(trifluoromethyl)phenyl]-1H-1,2,4-triazol-3-yl}formamido)-5-(3,3-difluoropiperidin-1-yl)pentanoic acid;
(3S)—N-cyclobutyl-3-({2-cyclopentyl-1-[2-(trifluoromethyl)phenyl]-1H-imidazol-4-yl}formamido)-5-(3,3-difluoropiperidin-1-yl)pentanamide;
(3S)-3-({2-cyclopentyl-1-[2-(trifluoromethyl)phenyl]-1H-imidazol-4-yl}formamido)-5-(3,3-difluoropiperidin-1-yl)-N-methyl-N-(1,3-thiazol-2-yl)pentanamide;
(3S)-3-(1-{5-cyclopentyl-1-[2-(trifluoromethyl)phenyl]-1H-1,2,4-triazol-3-yl}-N-methylformamido)-5-(3,3-difluoropiperidin-1-yl)-N-methyl-N-(1,3-thiazol-2-yl)pentanamide;
(3S)-3-{[4-(2-chlorophenyl)-1-methyl-5-(2-methylpropyl)-1H-imidazol-2-yl]formamido}-5-(3,3-difluoropiperidin-1-yl)pentanoic acid;
(3S)-3-{[4-(2-chlorophenyl)-1-methyl-5-(2-methylpropyl)-1H-imidazol-2-yl]formamido}-5-(3,3-difluoropiperidin-1-yl)-N-methyl-N-(1,3-thiazol-2-yl)pentanamide;
(3S)-3-{[4-(2-chlorophenyl)-1-methyl-5-(2-methylpropyl)-1H-imidazol-2-yl]formamido}-N-cyclobutyl-5-(3,3-difluoropiperidin-1-yl)pentanamide;
(3S)-3-({1-cyclopentyl-5-[3-(trifluoromethyl)pyridin-2-yl]-1H-1,2,4-triazol-3-yl}formamido)-5-(3,3-difluoropiperidin-1-yl)pentanoic acid;
(3S)-3-({5-cyclopentyl-1-[2-(trifluoromethyl)pyridin-3-yl]-1H-1,2,4-triazol-3-yl}formamido)-5-(3,3-difluoropiperidin-1-yl)pentanoic acid;
(3S)—N-cyclobutyl-3-({1-cyclopentyl-5-[3-(trifluoromethyl)pyridin-2-yl]-1H-1,2,4-triazol-3-yl} formamido)-5-(3,3-difluoropiperidin-1-yl)pentanamide;

(3S)—N-cyclobutyl-3-({5-cyclopentyl-1-[2-(trifluoromethyl)pyridin-3-yl]-1H-1,2,4-triazol-3-yl} formamido)-5-(3,3-difluoropiperidin-1-yl)pentanamide;

(3S)—N-cyclobutyl-3-({1-cyclopentyl-5-[2-(trifluoromethyl)pyridin-3-yl]-1H-1,2,4-triazol-3-yl} formamido)-5-(3,3-difluoropiperidin-1-yl)pentanamide;

(2S)-2-({5-cyclopentyl-1-[2-(trifluoromethyl)phenyl]-1H-1,2,4-triazol-3-yl} formamido)-N-(2-methoxyethyl)-N-methyl-4-phenylbutanamide;

(2S)-2-({1-cyclopentyl-5-[2-(trifluoromethyl)phenyl]-1H-1,2,4-triazol-3-yl}formamido)-N-(2-methoxyethyl)-N-methyl-4-phenylbutanamide;

(3S)-3-({5-cyclopentyl-1-[2-(trifluoromethyl)phenyl]-1H-1,2,4-triazol-3-yl} formamido)-5-(3,3-difluoropyrrolidin-1-yl)pentanoic acid;

5-cyclopentyl-N-[(2S)-4-(3,3-difluoropiperidin-1-yl)-1-(1H-1,2,3,4-tetrazol-5-yl)butan-2-yl]-1-[2-(trifluoromethyl)phenyl]-1H-1,2,4-triazole-3-carboxamide;

(3S)-3-({2-cyclopentyl-1-[2-(trifluoromethyl)phenyl]-1H-imidazol-4-yl} formamido)-5-(3,3-difluoropiperidin-1-yl)pentanoic acid, or a pharmaceutically acceptable salt thereof.

6. A pharmaceutical composition comprising at least one pharmaceutically acceptable excipient and a therapeutically effective amount of the compound of claim 1.

7. The pharmaceutical composition of claim/1, wherein the therapeutically effective amount is an amount effective for treating blood pressure, asthma, cardiomyopathy, diabetes, dyslipidemia, hypertension, inflammation, liver disease, metabolic disorder, neurodegenerative disease, obesity, preeclampsia, or renal dysfunction.

8. A method of treatment of an apelin receptor (APJ) related disorder comprising administering a therapeutically effective amount of the compound of claim 1, or a pharmaceutically acceptable salt thereof.

9. The method of claim 8, wherein the therapeutically effective amount is an amount effective for treating asthma, cardiomyopathy, diabetes, dyslipidemia, hypertension, inflammation, liver disease, metabolic disorder, neurodegenerative disease, obesity, preeclampsia, or renal dysfunction.

10. The method of claim 9, wherein
   (i) the hypertension is a pulmonary arterial hypertension;
   (ii) the liver disease is an alcoholic liver disease, a toxicant-induced liver disease or a viral-induced liver disease; or
   (iii) the renal dysfunction is a polycystic kidney disease.

11. The method of claim 8, further comprising administering one or more of an α-blocker, an angiotensin converting enzyme (ACE) inhibitor, an angiotensin-receptor blocker (ARB), a β-blocker, a calcium channel blocker, and a diuretic.

12. The method of claim 8, wherein the therapeutically effective amount is an amount effective for the treatment of a vein-related disorder.

13. The method of claim 12, wherein the vein-related disorder is an angioma, a venous insufficiency, a stasis or a thrombosis.

14. The method of claim 8, wherein the therapeutically effective amount is an amount effective for the treatment to reduce the likelihood of HIV-related neurodegeneration.

15. A pharmaceutical composition comprising at least one pharmaceutically acceptable excipient and a therapeutically effective amount of the compound of claim 5.

16. The pharmaceutical composition of claim 15, wherein the therapeutically effective amount is an amount effective for treating blood pressure, asthma, cardiomyopathy, diabetes, dyslipidemia, hypertension, inflammation, liver disease, metabolic disorder, neurodegenerative disease, obesity, preeclampsia, or renal dysfunction.

17. A method of treatment of an apelin receptor (APJ) related disorder comprising administering a therapeutically effective amount of the compound of claim 5, or a pharmaceutically acceptable salt thereof.

18. The method of claim 17, wherein the therapeutically effective amount is an amount effective for treating asthma, cardiomyopathy, diabetes, dyslipidemia, hypertension, inflammation, liver disease, metabolic disorder, neurodegenerative disease, obesity, preeclampsia, or renal dysfunction.

19. The method of claim 18, wherein
   (i) the hypertension is a pulmonary arterial hypertension;
   (ii) the liver disease is an alcoholic liver disease, a toxicant-induced liver disease or a viral-induced liver disease; or
   (iii) the renal dysfunction is a polycystic kidney disease.

20. The method of claim 17, further comprising administering one or more of an α-blocker, an angiotensin converting enzyme (ACE) inhibitor, an angiotensin-receptor blocker (ARB), a β-blocker, a calcium channel blocker, and a diuretic.

* * * * *

UNITED STATES PATENT AND TRADEMARK OFFICE
CERTIFICATE OF CORRECTION

PATENT NO. : 11,926,612 B2
APPLICATION NO. : 16/341597
DATED : March 12, 2024
INVENTOR(S) : Scott P. Runyon et al.

It is certified that error appears in the above-identified patent and that said Letters Patent is hereby corrected as shown below:

In the Claims
Column 80, Line 40, delete "$C_1$-s alkyl" and insert therefor -- $C_{1-8}$ alkyl --

Signed and Sealed this
Twenty-first Day of May, 2024

Katherine Kelly Vidal
*Director of the United States Patent and Trademark Office*